US011253749B2

(12) United States Patent
Lynch

(10) Patent No.: US 11,253,749 B2
(45) Date of Patent: *Feb. 22, 2022

(54) IDEAL TARGET WEIGHT TRAINING RECOMMENDATION SYSTEM AND METHOD

(71) Applicant: James Thurston Lynch, Bay Harbor Islands, FL (US)

(72) Inventor: James Thurston Lynch, Bay Harbor Islands, FL (US)

(73) Assignee: RELIANCE CAPITAL ADVISORS LLC, Coral Gables, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/908,687

(22) Filed: Jun. 22, 2020

(65) Prior Publication Data

US 2021/0121740 A1 Apr. 29, 2021

Related U.S. Application Data

(63) Continuation-in-part of application No. 16/667,879, filed on Oct. 29, 2019, now Pat. No. 10,688,345.

(51) Int. Cl.
*A63B 24/00* (2006.01)
*A63B 21/072* (2006.01)
(Continued)

(52) U.S. Cl.
CPC ...... *A63B 24/0075* (2013.01); *A63B 21/0726* (2013.01); *A63B 23/0494* (2013.01);
(Continued)

(58) Field of Classification Search
CPC ............ A63B 24/0075; A63B 21/0726; A63B 23/0494; A63B 23/1281; G06F 16/26; G06F 3/0484; G16H 20/30; G16H 50/30
See application file for complete search history.

(56) References Cited

U.S. PATENT DOCUMENTS 6,795,793 B2 9/2004 Shayegan et al.
7,063,644 B2 6/2006 Albert et al.
(Continued)

FOREIGN PATENT DOCUMENTS

WO 2006042415 A1 4/2006
WO 2006042420 A1 4/2006

*Primary Examiner* — Sundhara M Ganesan
(74) *Attorney, Agent, or Firm* — Mark C. Johnson; Dalal Johnson

(57) ABSTRACT

An ideal target weight training recommendation method ascertains a user's ideal target weight with a user-data algorithm that is operable to approximate an available weight value for a user to utilize for a given target weight training recommendation in addition to generating a rate in which a user's muscle fatigues. To do so, the user generates initial completed repetitions until the muscles fatigue. A baseline strength value is calculated with the initial completed repetitions and a baseline strength coefficient. A baseline strength value is created and used in calculating ideal target weight values. A y-intercept approximate functions involving user-selected desired target repetition values. The user manipulates a resistance structure associated with the ideal target weight values and said values are rounded to the nearest whole number. The user-selected desired target repetition values generate a second completed repetition values for subsequent sets for adjustment of a strength curve.

21 Claims, 13 Drawing Sheets

(51) Int. Cl.
  *A63B 23/04* (2006.01)
  *G06F 16/26* (2019.01)
  *G06F 3/0484* (2013.01)
  *G16H 20/30* (2018.01)
  *G16H 50/30* (2018.01)
  *A63B 23/12* (2006.01)

(52) U.S. Cl.
  CPC ........ *A63B 23/1281* (2013.01); *G06F 3/0484* (2013.01); *G06F 16/26* (2019.01); *G16H 20/30* (2018.01); *G16H 50/30* (2018.01)

(56) References Cited

U.S. PATENT DOCUMENTS

| | | |
|---|---|---|
| 8,920,287 B2 | 12/2014 | Doshi et al. |
| 9,125,620 B2 | 9/2015 | Walke et al. |
| 10,265,581 B2 | 4/2019 | O'Connor |
| 2008/0248926 A1* | 10/2008 | Cole .................. A63B 21/0628 482/5 |
| 2009/0075791 A1* | 3/2009 | Kissel .................. A63B 21/063 482/93 |
| 2010/0317489 A1* | 12/2010 | Flaction ............. A63B 24/0075 482/9 |
| 2011/0207581 A1* | 8/2011 | Flaction .................. A61B 5/22 482/8 |
| 2012/0058859 A1* | 3/2012 | Elsom-Cook .... A63B 21/00181 482/4 |
| 2018/0021616 A1* | 1/2018 | Orady ................ A63B 24/0087 482/5 |
| 2019/0009136 A1* | 1/2019 | Lee ........................ G16H 20/30 |
| 2019/0046839 A1* | 2/2019 | Jang .................... A61B 5/6804 |

* cited by examiner

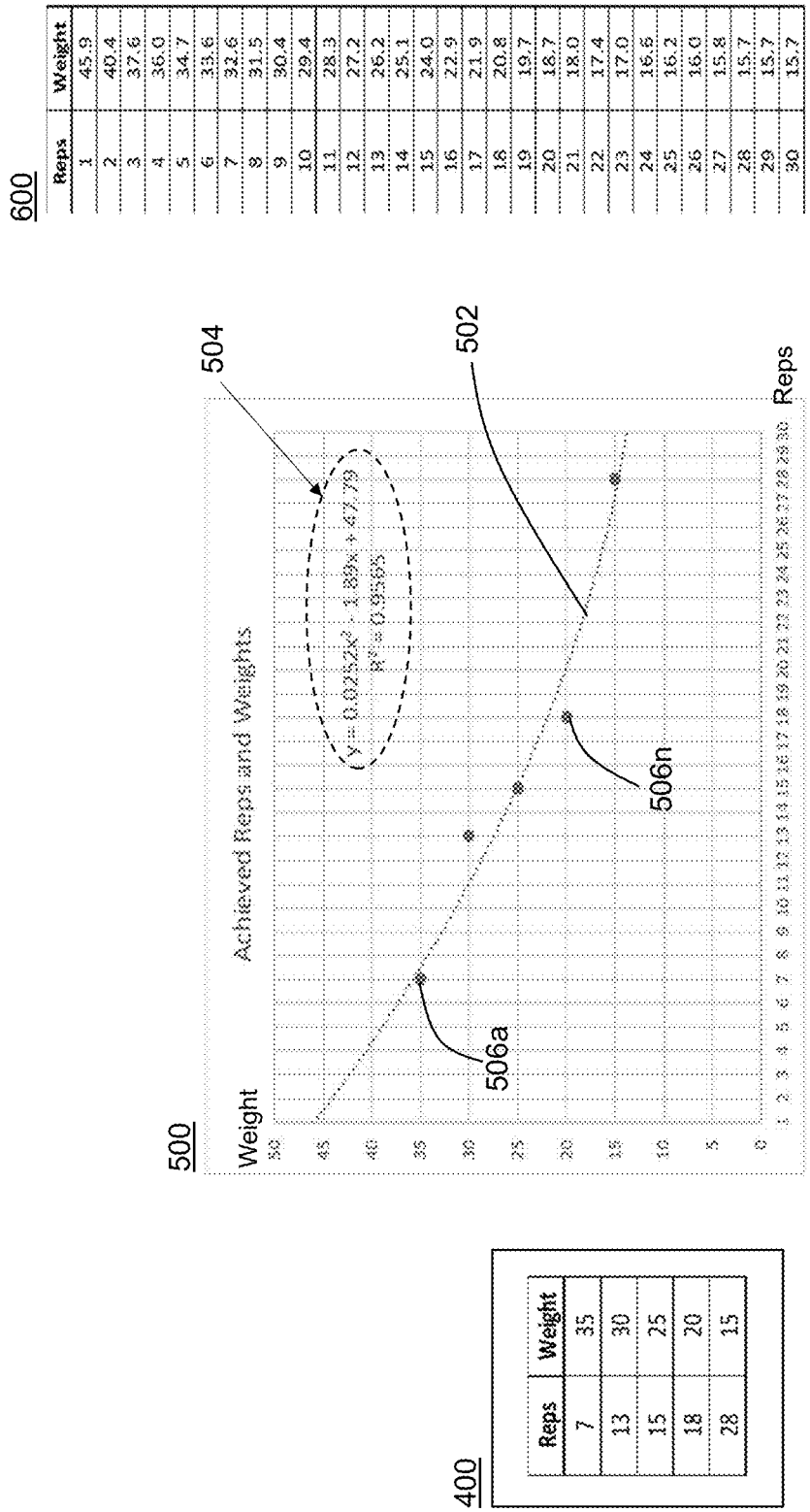

IDEAL TARGET WEIGHT TRAINING RECOMMENDATION SYSTEM AND METHOD

FIELD OF THE INVENTION

The present invention relates generally to exercise systems and methods, and, more particularly, relates to a system and method to generate a personalized strength curve for any exercise intended to train any muscle or muscle group and for recommending an ideal target resistance value, i.e., weight or resistance emulating a physical weight, to be employed by the user when performing the exercise.

BACKGROUND OF THE INVENTION

Typically, strength training exercises require manipulation of free weight bars and/or resistance equipment. Exercise regimes utilize resistance devices, such as dumbbells, barbells, resistance bands, isometric exercise devices, strength training machines, and the like. Other strength exercises include pull ups, push-ups, and squats that use body weight to provide resistance force.

Generally, a strength curve is a model that shows how much force you can produce at the joint angles throughout a range of motion for a given strength exercise routine or exercise. However, many known strength curves and workout plans with suggested exercise sets and repetitions (also referred to herein as "rep" or "reps" (plural)) recommendation models fail to indicate or suggest the ideal target weight or resistance to use or to sufficiently or adequately adapt to a wide variety of users over most, if not all, exercise routines.

The strenuous exercise of a muscle during a training session, with repeated reps and groupings of reps (referred to as "set" or "sets"), progressively develops fatigue and muscle fiber distress limiting the muscles ability achieve the same number of repetitions completed at the beginning of the exercise. The rate at which any given muscle loses strength is unique to the person and can change over time as the muscle gains or loses resistance. Generally, the more physically fit a person becomes, the slower his/her muscles will fatigue. Those known methods and devices developed to determine and evaluate muscle fatigue fail to accomplish the same in an effective and efficient manner.

Therefore, a need exists to overcome the problems with the prior art as discussed above.

SUMMARY OF THE INVENTION

The invention provides a muscle fatigue and required reps-to-beat target recommendation system and method that overcomes the hereinafore-mentioned disadvantages of the heretofore-known devices and methods of this general type and that works for any workout plan or exercise routine. The present invention can also be utilized in connection with a weight forecasting method that ascertains a user's ideal target weight by employing the use of one or more algorithms which define a strength curve (referred to as a "Lynch" curve) that includes a strength coefficient based on the maximum number of repetitions the user achieved until reaching fatigue/failure. Data was gathered from hundreds of actual weight and repetition (also referred to herein as a "rep" or "reps" (plural)) combinations from either male and female individuals with ages ranging from 18 to 65, novices, and athletes in order to generate an initial algorithm for either a male or female user, also referred to herein as a "Lynch Baseline Strength Curve." The Lynch Baseline Strength Curve has been tested and found to estimate the weight or resistance a user should use to reach the number of repetition he/she desires, with a high degree of accuracy, before failure. Often, the Lynch Baseline Strength Curve is automatically adjusted, enabling the personal characteristics of the user to adjust the curve to accommodate increases/decreases in strength.

However, the present invention provides a system and method of evaluating muscle fatigue testing to determine the rate a user's muscle fatigue by having the user periodically perform five sets for each exercise in his or her training program with the same weight, resting for exactly two minutes between sets. Each set must be performed to failure, until no additional repetitions can be performed. The number of repetitions achieved are then stored for evaluation and use.

With the foregoing and other objects in view, there is provided, in accordance with the invention, a weight-implemented method for recommending an ideal number of repetitions and an ideal target weight for a weight-training routine. The method includes an initial Step of providing at least one resistance structure with a weight or resistance value and operably configured to be manipulated, e.g., lifted or pulled, by a user for an exercise routine. Said another way, a computer-implemented and resistance-implemented method for recommending an ideal number of repetitions and an ideal target resistance value for an exercise routine is disclosed, with the method including providing at least one resistance structure with a resistance value and operably configured to be manipulated by a user for an exercise routine, providing a mobile electronic device of the user with a software application resident thereon, wherein the mobile electronic device operably configured to communicatively couple with a server computer over a network and the mobile electronic device of the user and the server computer each have a processor and memory operably coupled thereto. Further, the process will include initiating the software application to generate a user interface on the mobile electronic device and manipulating the at least one resistance structure by the user until a muscle fatigue is reached employing a recommended proper resistance structure use protocol for the exercise routine and ascertaining a number of initial completed repetitions associated with the resistance value. Further, the process will include utilizing the number of initial completed repetitions on the user interface of the software application to generate, with one of a plurality of user-data defined y-intercept approximation functions to generate a baseline strength value. Thereafter, the process will include utilizing the baseline strength value on the user interface of the software application to generate a plurality of ideal target weight values utilizing the one of the plurality of user-data defined y-intercept approximation functions, each involving a plurality of desired target repetition values. The process may also include manipulating by the user, during a plurality of subsequent sets involving the recommended proper resistance structure use protocol for the exercise routine, with the at least one resistance structure associated with the plurality of ideal target weight values, respectively, that are each rounded to the nearest whole number and for the greater of the plurality of user-selected desired target repetition values or until a muscle fatigue is reached to generate second completed repetition values for each of the plurality of subsequent sets.

In accordance with another embodiment of the present invention, the process may also include, after the plurality of desired target repetition values are generated with the plurality of ideal target weight values, generating a reps-to-beat (RTB) multiplier that is multiplied by each of the plurality of desired target repetition values and wherein said result of the multiplication respectively replacing the plurality of desired target repetition values before the user manipulates the at least one resistance structure in the plurality of subsequent sets.

In accordance with yet another embodiment of the present invention, the process may also include, directly after initiating the software application to generate the user interface on the mobile electronic device, selecting a user-desired strength objective on the user interface dictating an amount for the number of initial completed repetitions associated with the resistance value.

In accordance with a further embodiment of the present invention, the process may also include the user-desired strength objective includes various targeted repetition ranges different from one another on the user interface, wherein the amount for the number of initial completed repetitions associated with the resistance value of a median value within each respective targeted repetition ranges.

In accordance with another embodiment of the present invention, the process may also include utilizing the number of initial completed repetitions on the user interface of the software application to generate, with one of the plurality of user-data defined y-intercept approximation functions, a baseline strength coefficient, wherein the resistance value divided by the baseline strength coefficient to generate the baseline strength value.

In accordance with another embodiment of the present invention, the process may also include the generated plurality of ideal target weight values utilizing the one of the plurality of user-data defined y-intercept approximation functions are user-selected.

The present invention may also include a computer-implemented and resistance-implemented method for recommending an ideal number of repetitions and an ideal target resistance value for an exercise routine, with the method including providing at least one resistance structure with a resistance value and operably configured to be manipulated by a user for an exercise routine and providing a mobile electronic device of the user with a software application resident thereon, wherein the mobile electronic device is operably configured to communicatively couple with a server computer over a network and the mobile electronic device of the user and the server computer each having a processor and memory operably coupled thereto. Further the process may include initiating the software application to generate a user interface on the mobile electronic device and manipulating the at least one resistance structure by the user until a muscle fatigue is reached employing a recommended proper resistance structure use protocol for the exercise routine and ascertaining a number of initial completed repetitions associated with the resistance value. Further the process may include utilizing the number of initial completed repetitions on the user interface of the software application to generate, with one of a plurality of user-data defined y-intercept approximation functions to generate a baseline strength value and utilizing the baseline strength value on the user interface of the software application to generate a plurality of ideal target weight values utilizing the one of the plurality of user-data defined y-intercept approximation functions, each involving a plurality of desired target repetition values. Additionally, the process may include after the plurality of desired target repetition values are generated with the plurality of ideal target weight values, generating a reps-to-beat (RTB) multiplier that is multiplied by each of the plurality of desired target repetition values and wherein said result of the multiplication respectively replacing the plurality of desired target repetition value. Thereafter, the process may include manipulating by the user, during a plurality of subsequent sets involving the recommended proper resistance structure use protocol for the exercise routine, with the at least one resistance structure associated with the plurality of ideal target weight values, respectively, that are each rounded to the nearest whole number and for the greater of the plurality of user-selected desired target repetition values or until a muscle fatigue is reached to generate second completed repetition values for each of the plurality of subsequent sets.

Although the invention is illustrated and described herein as embodied in a ideal target weight training recommendation system and method, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time. Also, for purposes of description herein, the terms "upper", "lower", "left," "rear," "right," "front," "vertical," "horizontal," and derivatives thereof relate to the invention as oriented in the figures and is not to be construed as limiting any feature to be a particular orientation, as said orientation may be changed based on the user's perspective of the device. Furthermore, there is no intention to be bound by any expressed or implied theory presented in the preceding technical field, background, brief summary or the following detailed description.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the free weight structure. The terms "program," "software application," and the like as used herein, are defined as a sequence of instructions designed for execution on a computer system. A "program," "computer program," or "software application" may include a subroutine, a function, a procedure, an object method, an object implementation, an executable application, an applet, a servlet, a source code, an object code, a shared library/dynamic load library and/or other sequence of instructions designed for execution on a computer system.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

FIG. 4 is an exemplary look up table, referencing actual data points that represent the practical application of weight values during the weight training exercise, in accordance with the present invention;

FIG. 5 is an exemplary strength curve graph with a Lynch Strength Curve, in accordance with the present invention;

FIG. 6 is the look up table for the strength curve graph shown in FIG. 5, in accordance with the present invention;

DETAILED DESCRIPTION

Figure 1:
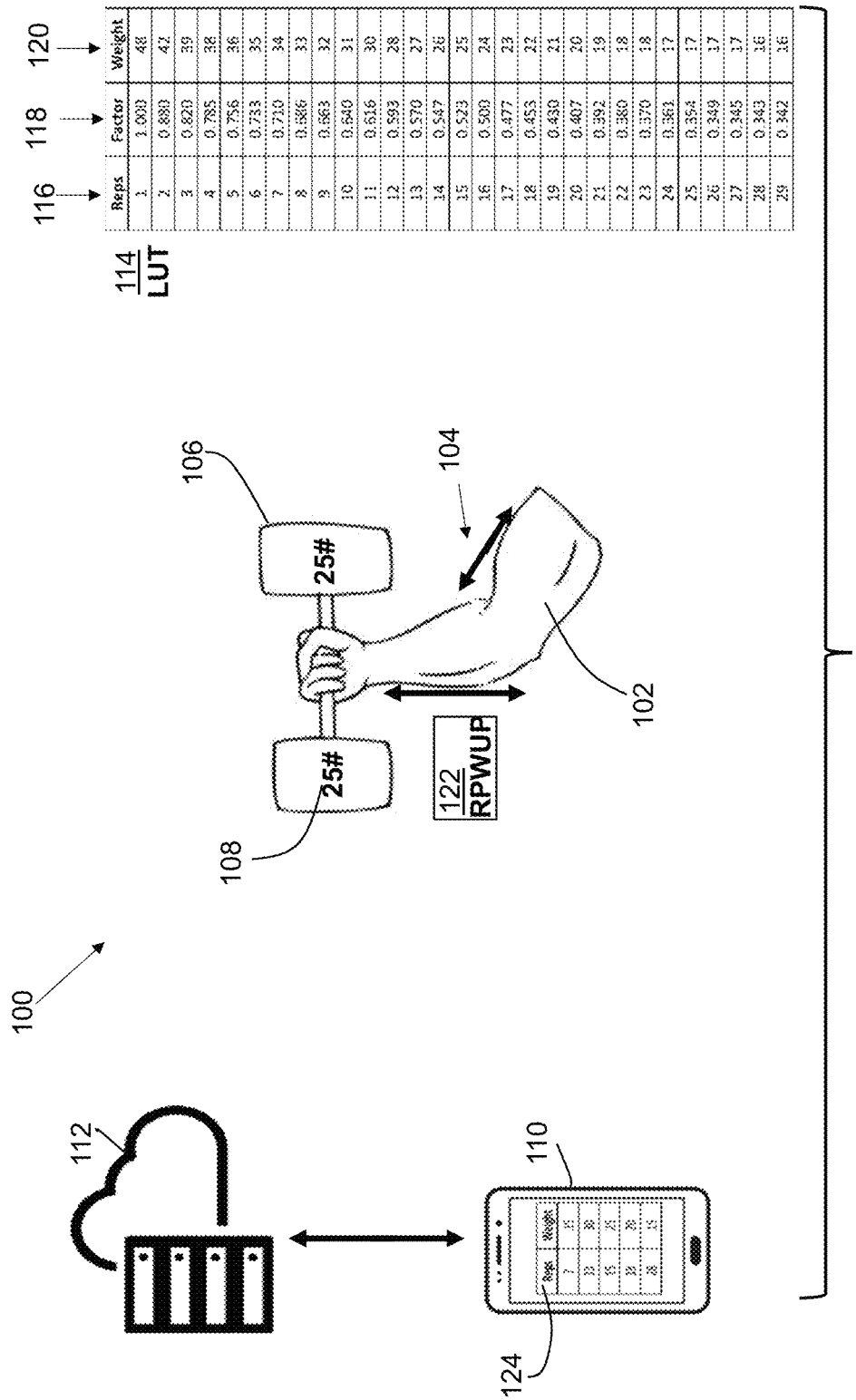
FIG. 1 is a block diagram of an exemplary weight-implemented system for recommending an ideal number of repetitions and an ideal target weight for a weight-training routine, in accordance with the present invention.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient ideal target weight training recommendation system 100 and method 1400. Embodiments of the invention work to ascertain a user's ideal target weight by employing the use of one or more user-data defined (also referred to as "user-defined") algorithms that includes a strength coefficient based on weight repetitions until a user's muscles reach fatigue.

In additional embodiments, the ideal target weight training recommendation system 100 and method 1400 progresses through three stages of development in order to achieve a unique and personalized strength curve for any muscle or muscle group the user chooses to develop. The personalized strength curve evolves and changes form as the user's strength changes. This continual adjustment of the user's exercise strength curve is critical in order to quickly adjust to increases, or decreases in the muscle's strength, thus permitting the user to maximize the result of his/her workouts.

Referring now to FIG. 1, one embodiment of the system 100 is shown in a block diagram view. FIG. 1 shows several advantageous features of the present invention, but, as will be described below, the invention can be provided in several shapes, sizes, combinations of features and components, and varying numbers and functions of the components. The first example of the system 100 and 1400 includes a free weight structure 106 or resistance mechanism; a mobile electronic device 110 with a software application 124 resident thereon communicatively coupled with a server computer 112 over a network; and a look-up table 114 (LUT) that references a number of repetitions 104 (reps) and a baseline factor 118.

An algorithm provides a formula that process the data points for the reps 104 and baseline factor to derive a preliminary weigh value 108 of the free weight structure 106. A user 102, which may include a person performing weight training exercises, operates the free weight structure 106 based on calculated preliminary weigh values 108 and reps 104. As the user's 102 strength increases/decreases, the system 100 recalculates the preliminary weigh value 108. A subsequent weigh value 108 and reps 104 are calculated for use during exercise. In this manner, the system 100 produces an evolving, customized weight training program for the user 102.

The user 102 initially determines an initial exercise. The exercise may include, without limitation, a bicep curl or a leg curl with a 90° motion, performed on a free weight structure 106 or resistance mechanism. The user 102 then selects a preliminary weigh value 108 for the free weight structure 106. The user 102 performs as many reps 104 as possible with the weigh value 108 until fatigue sets in, and it is not possible to continue.

Additionally, as referenced in FIG. 1, the system 100 utilizes a look-up table (LUT) 114. The LUT 114 is defined by columns containing data for reps 116, a base line factor 118, and a derived preliminary weigh value 120. The LUT 114 is used as a reference to determine a first approximation of a Y-intercept of the combination of weigh values 108 and reps 104. Based on the Y-intercept value, the LUT 114 projects the value of the preliminary weight or resistance value 108 for use in subsequent test sets of the weight training exercise.

Once the weigh value 108 is derived from the reps 116 and base line factor 118 referenced in the LUT 114, the user 102 commences with the weight training exercise, performing as many reps 104 as possible until failure or fatigue prevents continuing the repetitions. During this exercise, the user 102 exercises with a weigh value 108 of the free weight structure 106 derived from the LUT 114. The user 102 performs reps 104 with the weigh value 108 until fatigue sets in, and it is not possible to continue with the reps 104. These actual reps 104 and weigh value 108 may be different than the initial reps 104 and weigh value 108 found in the LUT 114.

As a result of the weight exercises with the initial reps 104 and weigh value 108, the user 102 generates and records an actual rep 104 and weigh value 108. The actual reps 104 represent the reps 104 performed until fatigue does not allow the user 102 to continue with the initial weigh value 108 and reps 104. The user 102 uploads the actual reps 104 and weigh value 108 through the software application 124 for input into an algorithm. The system provides an algorithm that calculates a strength curve that factors in a baseline for the selected weight training exercise and the number of reps performing the weight resistance motion.

This creates an initial muscle strength baseline for the muscle to be trained. The muscle strength baseline is graphically referenced as a strength curve (see FIG. 5). The strength curve may include a model that shows how much force can be produced at the joint angles throughout a range of motion, i.e., a bicep exercise, a leg curl exercise up to 90°. In one non-limiting embodiment of the present invention, the strength curve comprises a Lynch Strength Curve known in the art.

The weigh value 108 and the number of repetitions is entered into the algorithm by uploading into the software application 124 on a mobile electronic device 110. For example, the user 102 selects 25 pounds, which is a weigh value 108 or resistance where 5 to 20 repetitions can be achieved using proper form, until reaching failure. The user 102 then executes as many reps 104 possible until reaching failure. If for example, the user 102 performs 15 reps 104, a weigh value 108 of 25 pounds at 15 reps 104 is performed and entered into the algorithm.

Additionally, user 102 information is uploaded into the algorithm. This additional information creates a database of user information. Exemplary user information may include, without limitation: Identification of the user and user information; Name of the exercise; Date and time each exercise set was initiated and ended, and the rest period between sets; Number of sets performed; Weights used in each set; and Reps achieved in each set. In one non-limiting embodiment, the system 100 provides an Administrator to regulate the uploaded data and the calculations performed by the algorithm.

Figures 2, 3:
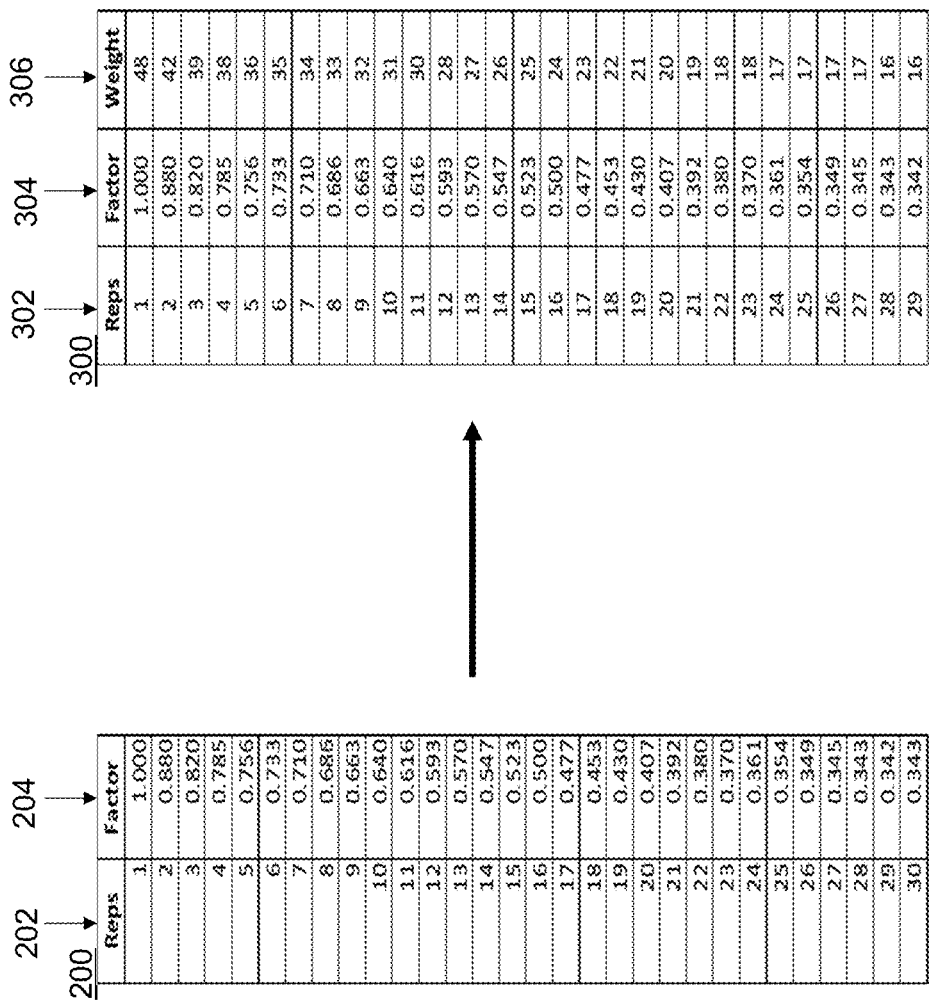
FIG. 2 is an exemplary look up table, defined by a repetitions value and a baseline factor, in accordance with the present invention.
FIG. 3 is an exemplary look up table, defined by a repetitions value, a baseline factor, and a weight or resistance value for a free weight structure, in accordance with the present invention.

The system 100 generates an LUT 200, shown in FIG. 2, which is derived from the Lynch Strength Curve baseline algorithm. The LUT 200 has columns for reps 202 and base line factors 204. The data 202, 204 in the LUT 200 is used to determine the first approximation of the user's Y-intercept of the combination of 25 lbs./15 Reps. Based on this value, an LUT 300 is generate. The LUT 300 also has columns for reps 302 and base line factors 304. Additionally, LUT 300 projects multiple preliminary weight or resistance value 306 to be used in the next four test sets of the weight training exercise (see FIG. 3). The LUT 300 provides the user with the weight or resistance value to achieve approximately 5, 10, 15 and 20 or 25 reps.

The algorithm calculates a Y-intercept as follows:
15 Reps Achieved=Factor: 0.523 (based on LUT 200)
25 lbs. Chosen Weight/0.523=47.8 lbs.=Y-intercept The system 100 applies the Y-intercept value of 47.8 lbs. to the Reps Factors in the Lynch Strength Curve LUT 300 to determine the weight values and targeted reps for the next four sets of the weight training exercise.

For example, as LUT 300 references in FIG. 3, extracted weights for 5, 10, 15, 20 and 25 reps are as follows:
5 Target Reps: 36 lbs.
10 Target Reps: 31 lbs.
15 Target Reps: 25 lbs.
20 Target Reps: 20 lbs.
25 Target Reps: 17 lbs.

This continual adjustment of the user's exercise strength curve is critical in order to quickly adjust to increase or decrease in the muscle's strength. The calculations by the algorithm enable optimal strength progression and muscle development; thereby allowing the user to maximize the result of weightlifting workouts.

It is significant to note that since the exact weights determined by the Lynch Strength Curve LUT 300 may not be available in the location the user is training, the available weight/resistance for the user may require adjusting by rounding up or down to the nearest next weight available. For example, on the first set test set the user achieved 15 Reps, the user performs sets targeting 5, 10, 20 and 25 Reps with the following weights:

5 Target Reps: 35 lbs.
10 Target Reps: 30 lbs.
15 Target Reps: 25 lbs.
20 Target Reps: 20 lbs.
25 Target Reps: 15 lbs.

At this point, the user commences exercising with these data points for reps and weight values. The user executes as many reps possible with the indicated weights until reaching failure for each of the four sets. For example, the actual reps achieved include:

For 35 lbs., 7 reps actually achieved;
For 30 lbs., 13 reps actually achieved;
For 20 lbs, 18 reps actually achieved; and
For 15 lbs, 28 reps actually achieved.

The user may then upload the actual reps 402 and actual weight values 404 into the software application, using the mobile electronic device. The actual data points represent the practical application of weight values during the weight training exercise and are recorded in an LUT 400 for further processing (see FIG. 4).

In one embodiment, an Administrator downloads the user's 102 exercise specific LUT to the user's software application on the mobile electronic device 110. The next time the user 102 trains this exercise this LUT will be the source to determine the weight to use for the exercise based on the number of targeted reps the user and the workout plan recommends. Once each set is completed, the user executes as many reps possible with the indicated weights until reaching failure for each of the four sets. The user 102 also uploads the actual reps and weight values performed into the software application after each set. Thus, with the actual reps and weight or resistance value uploaded, the algorithm calculates a second approximation of a Y-intercept. The second approximation is an improvement on the first approximation, since the actual reps possible until fatigue are being used.

In one possible embodiment of the calculation manifested in a strength curve graph 500, the subsequent calculation involves a quadratic, power or logarithmic equation 504, whichever achieves the highest R squared for each exercise using the datapoints of weight or resistance value and reps uploaded from the software application 124. An exemplary equation 504 is $y=0.0252x^2-1.89x+47.79$ $R^2=0.9565$. The Y-intercept value of $X=1$ in the polynomial, power or logarithmic equation 504 is then multiplied by the factors for each of the 1 to 30 repetition values in the Lynch Baseline Strength Curve LUT 500 to determine the second approximation of the amount of weight to use in order to achieve the desired number of repetitions before reaching failure. The strength curve 502 and data points 506a-n for these calculations is referenced in FIG. 5.

The second approximation of the weight or resistance value to be used is downloaded back to the mobile electronic device for weight training use. In this manner, the strength curve is constantly adjusted to factor in increases/decreases in strength. As the weight training exercise is performed and the user's strength increases, the updated weight or resistance value and reps data is uploaded to the user's database. The algorithm continues recalculating the Y-intercept value of $X=1$ in the polynomial, power or logarithmic equation, whichever returns the highest R squared. And a new exercise specific LUT 600 is generated and downloaded to the mobile electronic device for weight training use (see FIG. 6). The new exercise specific LUT 600 displays the updated reps and weight or resistance value that the user can incorporate into the weight lifting exercise.

Figure 7:
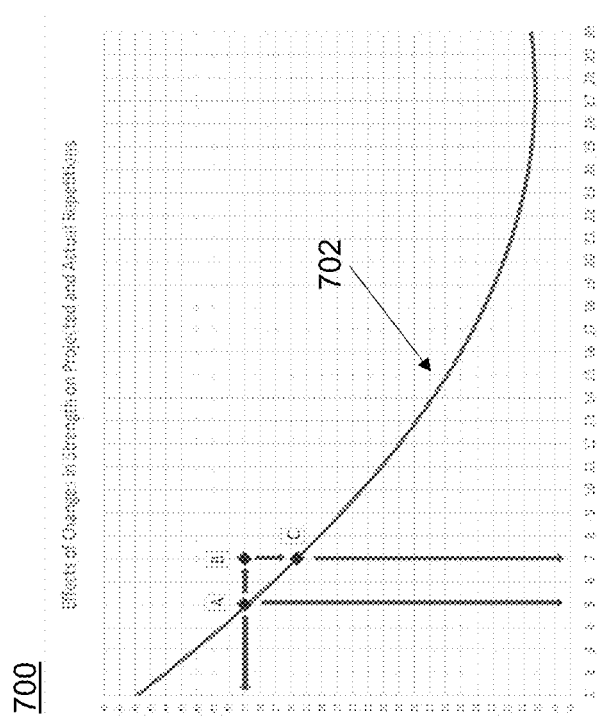
FIG. 7 is a first strength curve graph, showing the effects of changes in strength on projected and actual repetitions, in accordance with the present invention.

Turning now to FIG. 7, the system 100 provides a strength curve graph 700 graphically illustrating progress of the weightlifting workout. As the user's strength increases, the user can perform more repetitions with the same weight value. For example, as shown in graph 700, when the user began training, the user performed 5 Reps with 39 lbs. (A). As strength increased from the workouts, using the same 39 lb. weight or resistance value the user, on average over a number of workouts, can perform 7 repetitions before reaching failure (B). This change in strength moved the user's X, Y datapoint coordinates for this exercise down and to the right on the strength (C) on a Lynch Strength Curve 702.

Figure 8:
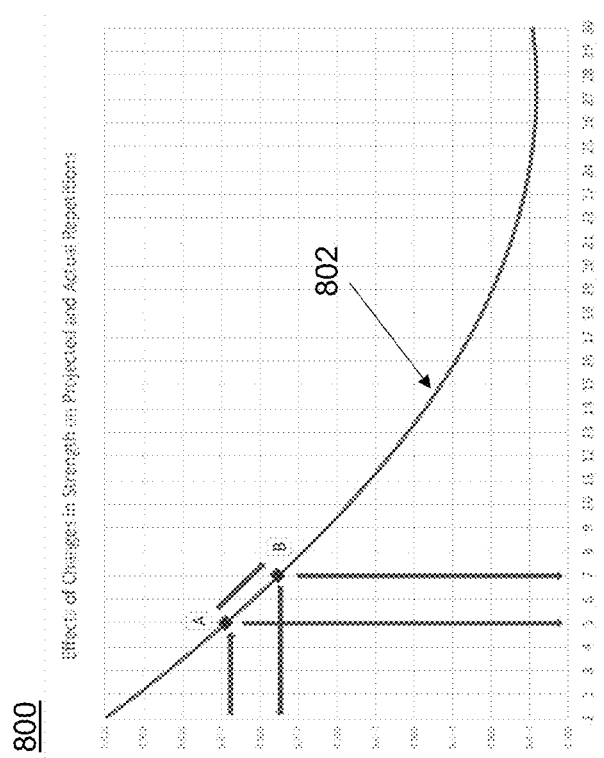
FIG. 8 is a second strength curve graph, showing the effects of changes in strength on projected and actual repetitions, in accordance with the present invention.

FIG. 8 shows a curve strength graph 800 as a result of the user's ability to increase from 5 Reps with 39 lbs. (A) to 7 Reps with the same 39 lbs. (B) the X, Y datapoint on a Lynch Strength Curve 802 moved down and to the right from Factor 0.844 to Factor 0.775. Based on this new data, the user's Y-intercept increased from 45.9 lbs. to 50.3 lbs. (39 lbs./0.775=50.3 lbs.), a 9.6% increase in strength. The new x=1, Y-intercept will now be used to calculate the new LUT and from it the appropriate heavier weight to be used the next time this exercise is performed.

Consequently, after five workout sessions of the weight training exercise are completed, the oldest datapoints related to the first workout, are discarded from the formula and replaced with the next, fifth workout datapoints. This continued cycle will ensure the data used in each new weight projection is updated to reflect the user's strength development.

The system 100 further includes a process of building a muscle strength database for each exercise using the strength curve. As the user continues to train and upload the results, the number of datapoints for each weight training exercise in the database increases. As the datapoints for each repetition number (X axis of the graph) reaches 12 or more, the user's individual physiology or strength related to one or more muscle groups differs from the baseline strength curve.

Such a difference can result from injury, a congenital condition, fast or low twitch muscle fiber composition, or existing superior physical conditioning found in advanced or professional athletes amongst many other variables. Thus, every time an individual user's performance diverges from the strength curve, the user's data is used to regenerate a customized strength curve for that specific condition.

Figure 9:
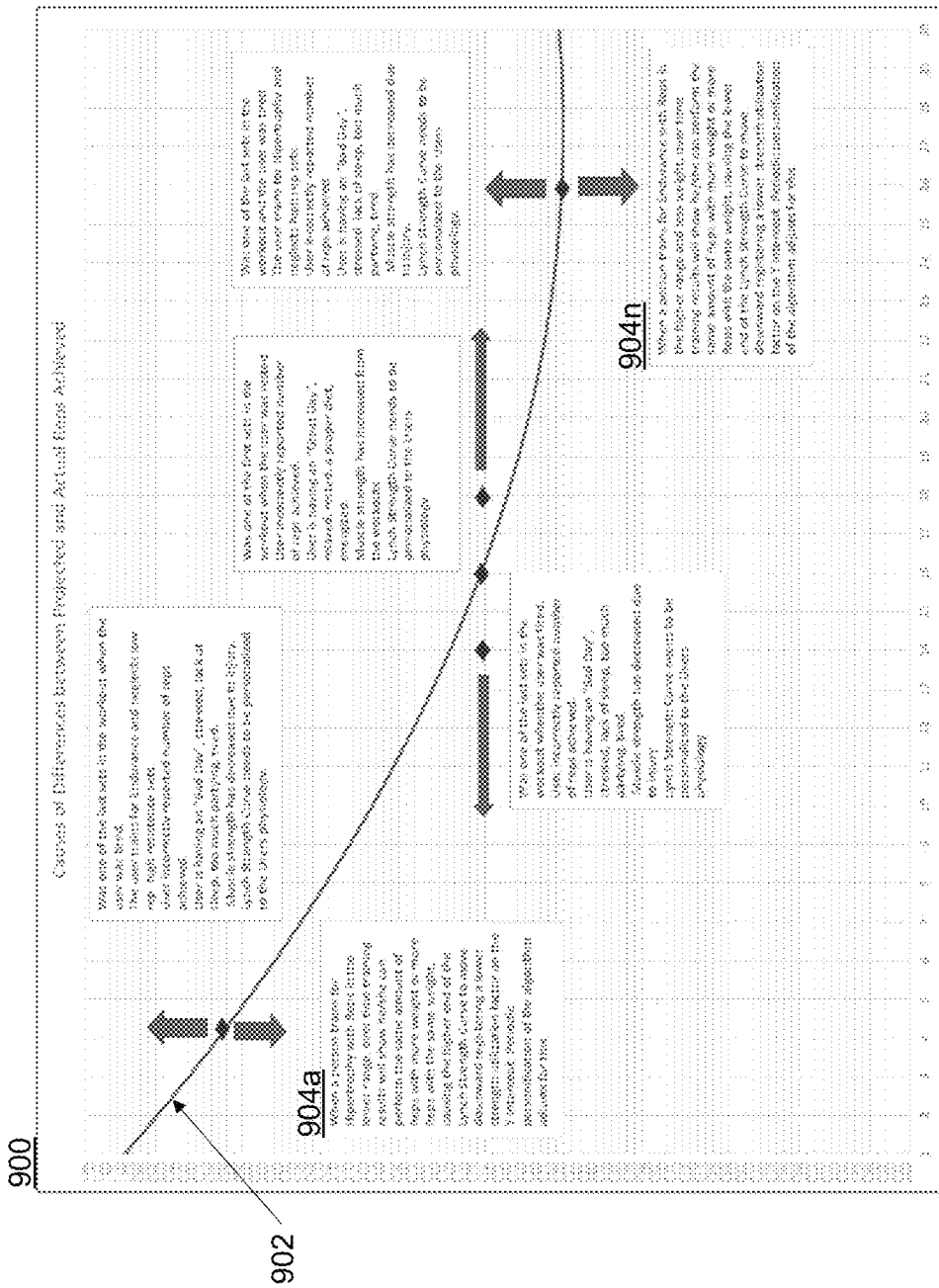
FIG. 9 is a strength curve chart that shows causes of differences between projected and actual reps achieved, in accordance with the present invention.

The system 100 further includes a process of customizing the strength curve for an individual or a group. FIG. 9 illustrates a strength curve chart 900 that shows causes 904a-n of differences between projected and actual reps achieved. Once twelve or more datapoints have been registered for targeted repetitions in the 1 to 30 range for a user's given exercise, any significant deviations from a strength curve baseline 902 are identified. The deviations between projected and actual reps achieved are used by the algorithm to calculate the next LUT and strength curve that adapts to the user's increasing/decreasing strength.

It is significant to note that the causes of possible deviations are numerous, with some of the principle ones are described in the graph 900. For example, in a first cause 904a of differences between projected and actual reps achieved; when the user trains for Hypertrophy with reps in the lower range, over time the training will show the user can perform the same amount of reps with more reps using the same weight value. This causes the higher end of the Lynch Strength Curve to move downward, registering a lower strength utilization factor on the Y-intercept. Further, periodic personalization of the algorithm adjusts for this specific cause of differences.

Once significant deviations are identified, the system 100 excludes the datapoints beyond one sample standard deviation from the Mean of the datapoints related to specific repetition numbers and recalculate the new Mean for that number of repetitions. This action ensures that statistically non-representative datapoints, (possibly registered incorrectly by the user, or being the result of when he/she did not continue repetitions until failure), do not adversely influence the calculation of a new Mean. Performing this process for five or more rep values (example: 5, 10, 15, 20 and 25 repetitions) enables a unique polynomial, power or logarithmic equation to be created for an individual or a specific group of individuals. As a result, a new LUT determines the proper weights to be used in performing that exercise.

Those skilled in the art will recognize that numerous personal factors on any given day can come to bear on a user performing reps, causing an increase or decrease on that training day, in the average maximum number of reps he/she performs until reaching failure. Stress, lack of sleep, a pulled muscle, a bad night sleep, improper nutrition, alcohol, bad form, too much partying or just a lack of enthusiasm to push for those last few reps. On the other hand, a user may be experiencing a great day, properly hydrated, motivated and ready to beat his record and exceed the average number of reps he/she performs for a given exercise.

Furthermore, it is understood in the art that the physiological makeup of a user may be determined by genetics, or prior physical condition and can change his/her ability to perform certain exercises. Age, sex, injuries, muscle composition, physical size, hormone levels, nutrition and many more characteristic make each person a unique individual, with no other alike in the world. No two people are physiologically alike, and no individual is the same from one day to the next. Strength training adds an additional variable that causes continual change in the body's ability to overcome resistance.

Those skilled in the art will recognize that the Lynch Baseline Strength Curve data was gathered from hundreds of actual weight and rep combinations from male and female individuals with ages ranging from 18 to 65, novices and athletes and has been tested and found to estimate the weight or resistance a user should use to reach the number of repetition he/she desires, with a high degree of accuracy. But, as everyone is different and his/her body is continually undergoing change, the Lynch Baseline Strength Curve and the system 100 used to automatically adjust the curve, enable the personal characteristics of an individual or a group to adjust the curve to their reality.

To exemplify how Lynch Strength Curve and its Functions are adjusted to an individual or groups' actual performance, 15 datapoints for three Target Rep's levels will be used; 5, 15 and 20 reps. Normally this process is uses five or more Target Rep levels, but for the purpose of simplification we will use only three. The new Target Reps and their respective Factors derived from the process below will be applied to a polynomial, power or logarithmic equation, or combinations thereof, to generate a personal strength curve for the user The testing system uses the actual number of reps achieved for one specific exercise by the user before reaching failure and the weight he/she used. For example, as referenced in strength curve graph 1000 of FIG. 10, in the case where the Five Rep Target was tested, the Lynch Baseline Strength Curve projected a Target Rep Factor 1002 of 0.756. The actual reps achieved varied each time the user performed the exercise, as can be seen in the Actual Reps column, or generated second completed repetition values 1006 in table 1004.

The Target Rep Factors 1008 related to the Actual Reps achieved are found in the Actual Rep Factor column. The arithmetic mean of the Target Rep Factors 1002 is 0.756, while the arithmetic mean of the Actual Rep Factor 1008 is 0.762; a small 4/10 of one percent difference indicating that on average the user's strength for repetitions in the 5 repetitions range are just slightly less than projected by the Lynch Baseline Strength Curve.

When the data from the table is graphed in graph 1000, the very small difference between what the Lynch Baseline Strength Curve projected 1002 and the Mean of the Actual Rep Factors 1008 is minute. The actual datapoints are blue. However small the difference, this new Factor for 5 Target Reps is utilized to develop a personalized strength curve algorithm and LUT for the user.

Figures 10, 11:
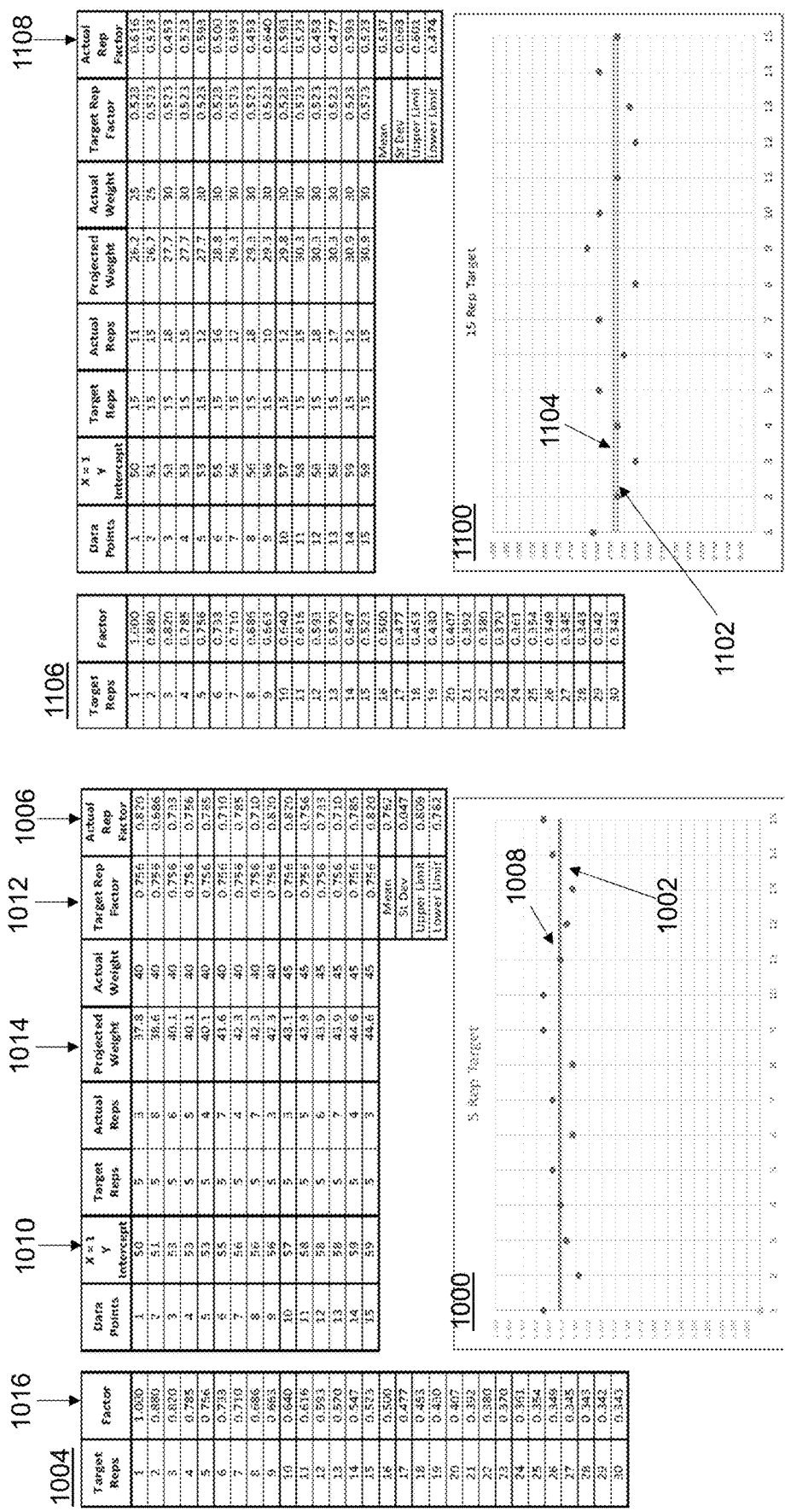
FIG. 10 is a first Lynch Baseline Strength Curve projecting a Target Rep Factor and an Actual Rep Factor, in accordance with the present invention.
FIG. 11 is a second Lynch Baseline Strength Curve projecting a Target Rep Factor and an Actual Rep Factor, in accordance with the present invention.

Turning now to FIG. 11, the Fifteen Rep Target is tested. Here, the Lynch Baseline Strength Curve projects a Target Rep Factor 1102 of 0.523. The actual reps achieved varied each time the user performed the exercise, as can be seen in the Actual Reps column in table 1106. The Target Rep Factors 1102 related to the Actual Reps achieved are found in the Actual Rep Factor column 1108. As graph 1100 references, the arithmetic Mean of the Target Rep Factors 1102 is 0.523, while the arithmetic mean of the Actual Rep Factor 1104 is 0.537; a small 2.7 percent difference indicating that the user's strength for repetitions in the 15 repetitions range are slightly less than projected by the Lynch Baseline Strength Curve.

When this data from the table is graphed, the very small difference between what the mean factor the Lynch Baseline Strength Curve projected 1102 and the mean of the Actual Rep Factors 1104 is visible. The actual datapoints are blue. However small the difference, the new Factor for 15 Target Reps is used in developing a personalized strength curve algorithm and LUT for the user.

Figure 12:
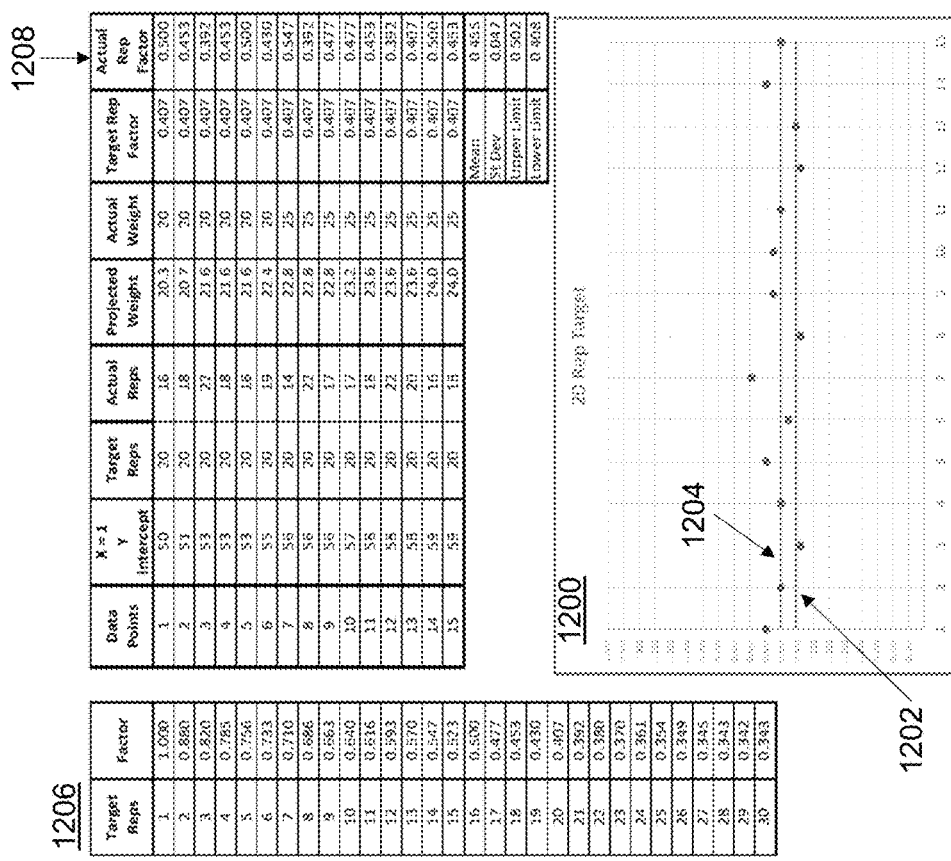
FIG. 12 is a third Lynch Baseline Strength Curve projecting a Target Rep Factor and an Actual Rep Factor, in accordance with the present invention.

Looking at FIG. 12, in the case where the Twenty Rep Target are tested, the Lynch Baseline Strength Curve, shown in graph 1200, projects a Target Rep Factor 1202 of 0.407. The Target Rep Factors related to the Actual Reps achieved are found in the Actual Rep Factor column 1208. The arithmetic mean of the Target Rep Factors 1202 is 0.407, while the arithmetic mean of the Actual Rep Factor 1204 is 0.455; an 11.8 percent difference indicating that the user's strength for repetitions in the 20 rep range are somewhat lower than the Lynch Baseline Strength Curve predicted, but still within the actual range of the datapoints.

When this data from table 1206 is graphed, the difference between what the mean factor the Lynch Baseline Strength Curve projected 1202 and the mean of the Actual Rep Factors 1204 can be seen. The actual datapoints are blue. The mean of the Actual Rep Factors for 20 target reps are utilized used in developing a personalized strength curve algorithm and LUT for the user.

Figure 13:
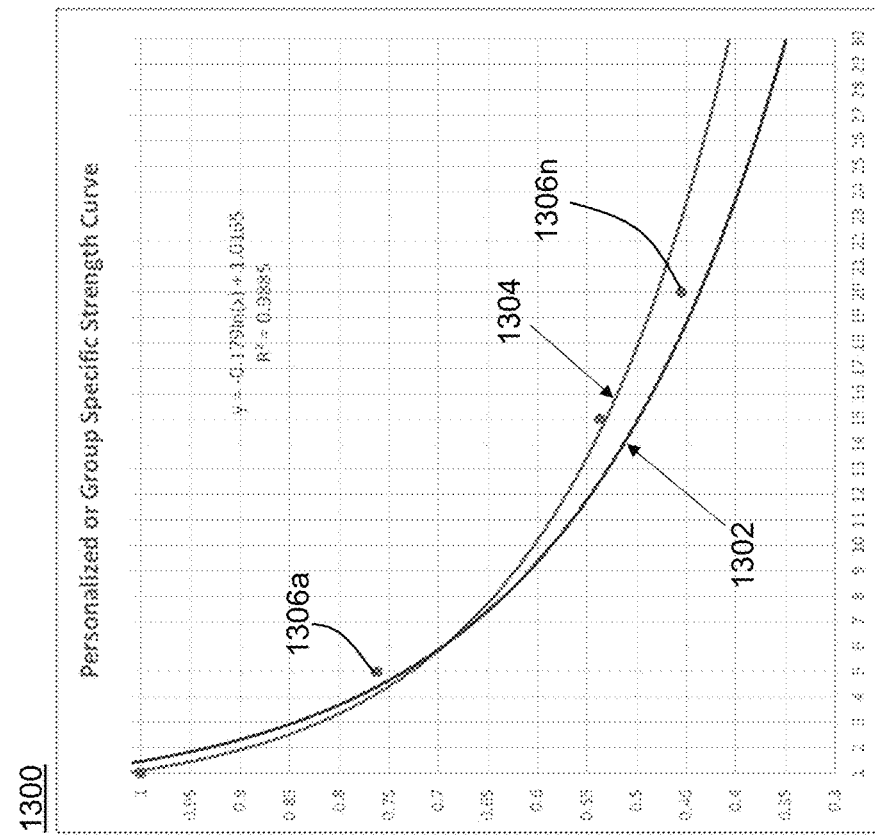
FIG. 13 is a strength curve graph having six or more adjusted new rep datapoints utilized to design a Personalized or Group Specific Strength Curve, in accordance with the present invention.

As shown in FIG. 13, the system 100 is also useful for comparing the Lynch Baseline Strength Curve to a new personalized or group specific strength curve. The strength curve graph 1300 illustrates six or more adjusted new rep datapoints 1306*a-n* are utilized to design a Personalized or Group Specific Strength Curve. In this example, for simplicity sake, the only data graphed is the data for the 1, 5, 15 and 20 repetition levels based on the aforementioned information. Curve 1302 on the graph 1300 is the Lynch Baseline Strength Curve 1304. The strength curve 1304 is a new Personalized or Group Specific Strength Curve.

In this situation, the algorithm which best fit the new data is a logarithmic curve with an R squared of 0.9885 based only of these four datapoints. With three more datapoints (especially for the 8, 12 and 25 rep values) which the new curve reduces the variance and generates a higher R squared. Interpreting the new curve 1304, when compared to the Lynch Baseline Strength Curve 1302, one could conclude that the new curve relates to a person or group training more for hypertrophy than for Endurance. At the low repetition range the new curve 1304 indicates that the user requires less strength on average to achieve up to 6 repetitions. Beyond 6 repetitions the user requires more strength than projected by the Lynch Baseline Strength Curve, on average, to achieve the higher repetition range.

A new LUT is then calculated by applying the new logarithmic curve and its respective Factor values on the Y axis and the related repetition numbers on the X axis. The LUT will be downloaded to the mobile electronic device and used to determine the weights to be used for the weight training exercise until any additional adjustment is made necessary in light of changes in the user performance.

Figure 14:
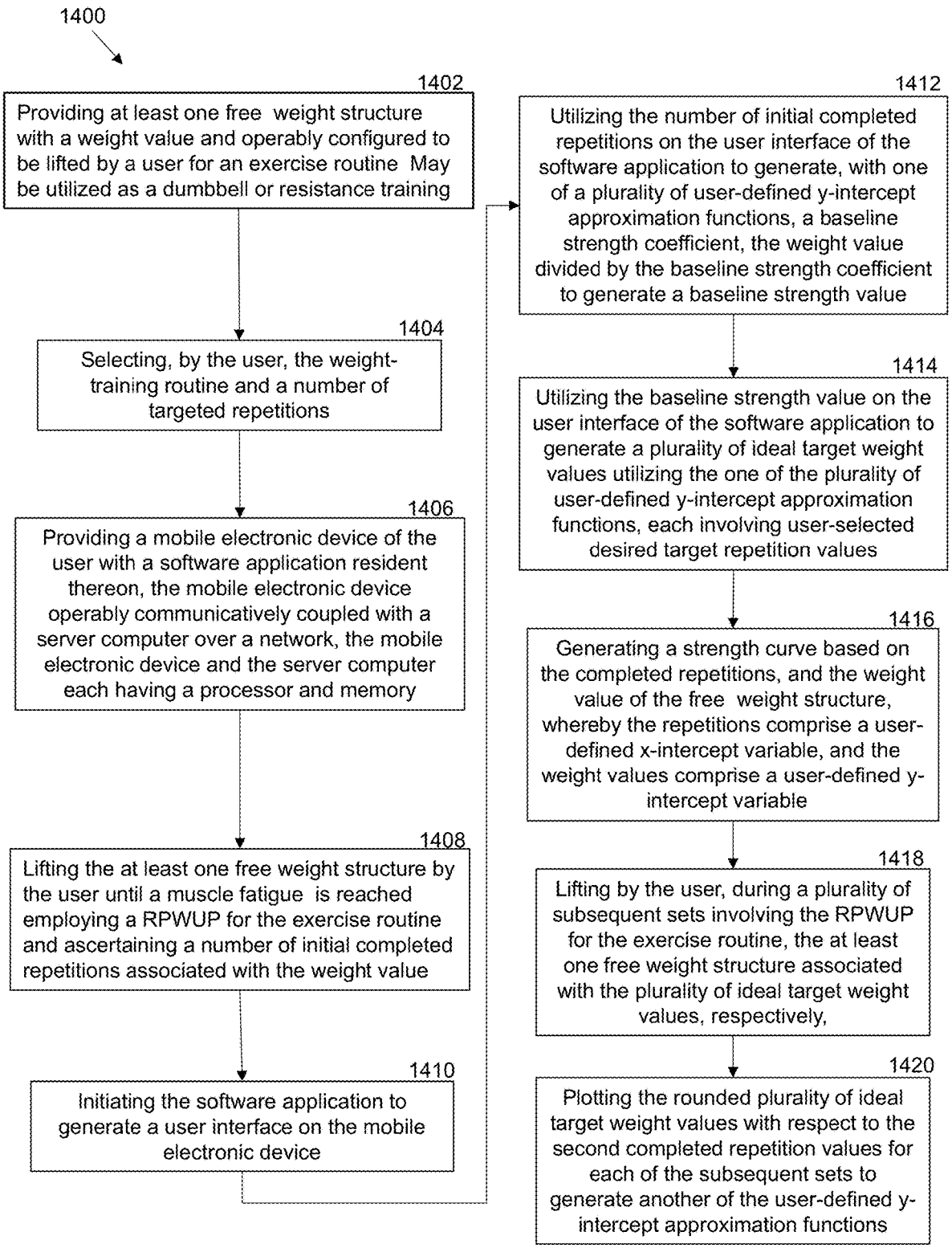
FIG. 14 is a flowchart diagram of an exemplary weight-implemented method for recommending an ideal number of repetitions and an ideal target weight for a weight-training routine, in accordance with the present invention.

FIG. 14 references a flowchart of an exemplary efficient ideal target weight training recommendation method 1400. FIGS. 1-13 will be described in conjunction with the process flow chart of FIG. 14. Although FIG. 14 shows a specific order of executing the process steps, the order of executing the steps may be changed relative to the order shown in certain embodiments. Also, two or more blocks shown in succession may be executed concurrently or with partial concurrence in some embodiments. Certain steps may also be omitted in FIG. 14 for the sake of brevity. In some embodiments, some or all of the process steps included in FIG. 14 can be combined into a single process.

The method 1400 has the objective of designing a personalized strength curve for any muscle or muscle groups the user 102 wants to develop (see FIG. 5). The strength curve 502 is used to project the weight or resistance to be used in a strength training exercise to achieve a desired number of targeted repetitions per set, at which point the muscle or muscle group will reach failure. Further, the method 1400 is operable with any weight or resistance exercise or workout plan.

For ideal results the method 1400 requires the user 102 to continue preforming repetitions of the exercise until reaching failure. The method 1400 progresses through three stages of development in order to achieve a unique and personalized strength curve for any muscle or muscle group the user chooses to develop. The personalized strength curve evolves and changes form as the user's strength changes. The curve automatically adapts to the user's strength progression and muscle development.

The method 1400 may include an initial Step 1402 of providing at least one free weight structure 106 with a weight or resistance value 108 and operably configured to be lifted by a user 102 for an exercise routine. Another Step 1404 comprises, selecting, by the user, the weight-training routine and a number of targeted repetitions 116. The weight-training routine may include, without limitation, a bicep curl motion using a dumbbell for an arm curl, or a 90° extension motion for a leg curl.

The method 1400 may further comprise a Step 1406 of providing a mobile electronic device 110 of the user with a software application 124 resident thereon, the mobile electronic device operably configured to communicatively couple with a server computer over a network, the mobile electronic device of the user and the server computer each having a processor and memory operably coupled thereto.

The mobile electronic device 110 may include, without limitation, a smart phone, a tablet, a laptop, and a processor.

A Step 1408 includes lifting the at least one free weight structure 106 by the user until a muscle fatigue is reached employing a recommended proper resistance structure use protocol 122 (RPRSUP) for the exercise routine and ascertaining a number of initial completed repetitions 116 associated with the weight or resistance value 120. The number of initial completed repetitions comprises 5 to 20 reps. For example, 5, 10, 15, and 20 reps can be performed to ascertain the weight value.

In one non-limiting embodiment, the RPRSUP 122 comprises a bicep curl motion using a dumbbell for an arm curl, or a 90° extension motion for a leg curl. However, in other embodiments, other types of weight or resistance exercises may be used with the present method 1400. In some embodiments, a Step 1410 comprises initiating the software application 124 to generate a user interface on the mobile electronic device 110.

A Step 1412 includes utilizing the number of initial completed repetitions on the user interface of the software application to generate, with one of a plurality of user-data defined y-intercept approximation functions 1010, a baseline strength coefficient 118, the weight or resistance value divided by the baseline strength coefficient 118 to generate a baseline strength value 1016. The user interface allows the user 102 to build a muscle strength database for each exercise using the strength curve. As the user continues to train and upload the results, the number of datapoints for each weight training exercise in the database increases. As the datapoints for each repetition number (X axis of the graph) reaches 12 or more, the user's individual physiology or strength related to one or more muscle groups differs from the baseline strength curve.

In some embodiments, user-data defined y-intercept approximation functions 1010 may include, without limitation, a logarithmic function, a quadratic function, and a power function. In other embodiments, the y-intercept approximation functions 1010 is a natural logarithmic function. In one non-limiting embodiment, the natural logarithmic function is $x\ln(ICR)+b$, wherein ICR is the number of initial completed repetitions associated with the weight value. In another embodiment, the baseline strength coefficient 118 is a baseline factor generated on the user interface of the software application with at least one of a LUT 114 and a completed repetition input field 400.

In some embodiments, a Step 1414 may include utilizing the baseline strength value 1016 on the user interface of the software application to generate a plurality of ideal target weight values 1014 utilizing the one of the plurality of user-data defined y-intercept approximation functions, each involving a plurality of user-selected desired target repetition values 1012. This includes a first approximation of the user's Y-intercept of the combination of 25 lbs./15 Reps and based on this value, projects preliminary weights to be used in the next four test sets of the exercise. An LUT derived from the Lynch Strength Curve baseline algorithm determines this first approximation. The LUT provides the user with the weight to achieve approximately 5, 10, 15 and 20 or 25 reps Another Step 1416 comprises generating a strength curve based on the completed repetitions, and the weight or resistance value of the free weight structure, whereby the repetitions comprise a user-defined x-intercept variable, and the weight values comprise a user-data defined y-intercept variable. The strength curve 502 is used to project the weight or resistance to be used in a strength training exercise to achieve a desired number of targeted repetitions per set, at which point the muscle or muscle group will reach failure. An exemplary LUT 600, and accompanying strength curve graph 500 are illustrated in FIGS. 5-6.

A final Step 1418 comprises lifting by the user, during a plurality of subsequent sets involving the RPRSUP for the exercise routine, the at least one free weight structure associated with the plurality of ideal target weight values 1014, respectively, that are each rounded to the nearest whole number and for the greater of the plurality of user-selected desired target repetition values or until a muscle fatigue is reached to generate second completed repetition values 1006 for each of the plurality of subsequent sets. The second completed repetition values 1006 are a second approximation of the amount of weight to use in order to achieve the desired number of reps before reaching failure.

To achieve the second completed repetition values 1006, the algorithm calculates a quadratic, power or logarithmic equation, whichever achieves the highest R squared for each exercise using the datapoints of weight and reps uploaded from the Users mobile app. The Y-intercept value of X=1 in the polynomial, power or logarithmic equation is then multiplied by the factors for each of the 1 to 30 rep values in the Lynch Baseline Strength Curve LUT to determine the second approximation of the amount of weight to use in order to achieve the desired number of reps before reaching failure. The one of a plurality of y-intercept approximation functions is a natural logarithmic function. In one embodiment, the natural logarithmic function is $x\ln(\text{ICR})+b$, wherein ICR is the number of initial completed repetitions associated with the weight value.

Another possible Step 1420 provided by the method 1400 comprises plotting the rounded plurality of ideal target weight values 1014 with respect to the second completed repetition values 1006 for each of the plurality of subsequent sets to generate another of the plurality of user-data defined y-intercept approximation functions 1010 dictated by a highest coefficient of determination.

In operation of the system 100 and method 1400, the user defines a user profile. The user profile includes:
Sex: Female
Age: 21
Level of present level of strength training activity:
1) Novice
2) Less than one year training
3) 1 to 3 years training
4) 3 to 5 years training
5) Over 5 years training The user may then choose a workout routine. This system and method can be applied to any exercise in any existing workout routine; endurance, strength hypotrophy, physical therapy, etc. In this example, the user's chosen exercise routine starts with a Dumbbell Curl to train the Biceps Brachii muscle and involves four sets of 20, 5, 15 and 10 repetitions.
Muscle to Train: Biceps Brachii
Exercise: Dumbbell Curl
Instruct the user on proper form to execute the exercise
Set 1 Target Reps: 20
Set 2 Target Reps: 5
Set 3 Target Reps: 15
Set 4 Target Reps: 10

The user's Baseline Strength Curve Algorithm is defined. Based on User Profile, determine which of the systems Baseline Strength Curve Algorithm to apply to the person's Workout Routine. In this example the user is a female, less than 30 years old and a novice to strength training, so the BSCA which will be applied to her training routine is:

Female/less than 30 Years/Novice: BSCA=$-0.18$ $\ln(\text{CR})+1.0212$

However, if the user was a male, less than 30 years old and a novice to strength training, the BSCA which would be applied to his training routine would have been:

Male/less than 30 Years/Novice: BSCA=$-0.17$ $\ln(\text{CR})+0.9602$

The user defines a Baseline Strength Coefficient (in this example, Dumbbell Curl). The first time a user chooses to use a new exercise in his/her workout routine he/she must execute a test set of reps to define his/her Baseline Strength Coefficient (BSC) for that exercise. This is done by picking a weight he/she is comfortable in using to achieve between 5 and 15 repetitions. Using proper form, the user performs as many repetitions with the chosen weight until the muscle reaches total fatigue (until the next repetition cannot be completed).

The female user in this example completed 15 Repetitions (CR) with a Weight of 15 lb. weight (W) until total fatigue set in. Her Baseline Strength Coefficient for the set of reps is therefore 0.5338

BSC=$-0.18 \ln(\text{CR})+1.0212$

BSC=$(-0.18 \ln(15)+1.0212)=0.5338$

The user defines a Baseline Strength Value for Exercise 1

BSV=$W$/BSC

BSC=$15/0.5338=28.103$

An Ideal Target Weight (ITW) for Exercise 1 Set 1 which has a Target Repetition (TR) of 20 Reps is determined:

ITW=BSC$\times(-0.18 \ln(\text{TR})+1.0212)$

ITW=$(15/0.5338\times(-0.18 \ln(20)+1.0212)$

ITW=$28.103\times0.4820=13.545$ lbs.

To perform the first set of first set of 20 Dumbbell Curl's, the user would ideally use a weight of 12.416 Lbs. As weights don't come in such minor weight increments, this ITW will be adjusted, as explained further in this example.

The user determines the Ideal Target Weight (ITW) for Exercise 1 Set 2 which has a Target Repetition (TR) of 5 Reps:

ITW=BSC$\times(-0.18 \ln(\text{TR})+1.0212)$

ITW=$(15/0.5338\times(-0.18 \ln(5)+1.0212)$

ITW=$28.103\times0.7315=20.557$ lbs.

To perform the first set of first set of 5 Dumbbell Curl's, the user would ideally use a weight of 20.557 Lbs. As weights don't come in such minor weight increments, this ITW will be adjusted, as explained further in this example.

The Ideal Target Weight (ITW) is determined for Exercise 1 Set 3 which has a Target Repetition (TR) of 15 Reps:

ITW=BSC$\times(-0.18 \ln(\text{TR})+1.0212)$

ITW=$(15/0.5338\times(-0.18 \ln(15)+1.0212)$

ITW=$28.103\times0.5338=13.545$ lbs.

To perform the first set of first set of 15 Dumbbell Curl's, the user would ideally use a weight of 13.545 Lbs. As weights don't come in such minor weight increments, this ITW will be adjusted, as explained further in this example.

The Ideal Target Weight (ITW) is determined for Exercise 1 Set 4 which has a Target Repetition (TR) of 10 Reps:

$$ITW = BSC \times (-0.18 \ln(TR) + 1.0212)$$

$$ITW = (15/0.5338 \times (-0.18 \ln(10) + 1.0212)$$

$$ITW = 28.103 \times 0.6067 = 17.051 \text{ lbs.}$$

To perform the first set of first set of 10 Dumbbell Curl's, the user would ideally use a weight of 17.051 Lbs. As weights don't come in such minor weight increments, this ITW will be adjusted, as explained further in this example.

The user may then choose a weight to use: Available Weight Used (AWU). Gyms do not have weights or resistance equipment to match the Ideal Target Weight (ITW) which is calculated down to decimals of a lb. Therefore, the user should choose the next higher weight available and record it as the Available Weight Used (AWU) when reporting the results of each set performed.

| Dumbbell Curl | ITW | AWU |
|---|---|---|
| Set 1, 20 Target Reps: | 12.416 | 12 |
| Set 2, 5 Target Reps: | 20.557 | 20 |
| Set 3, 15 Target Reps: | 13.545 | 15 |
| Set 4, 10 Target Reps: | 17.051 | 15 |

Whenever significant variations in a user group's performance differentiates from other user groups, the system 100 and method 1400 creates a new specific BSCA's for that specific group.

An exemplary workout routine involves three workouts per week and five exercises per workout. A week 1 and week 2 of weightlifting exercises has the same exercises but different repetition targets. Week 1 target reps 20, 5, 15 and 10 Reps. And week 2 target reps for the same exercises but with 10, 15, 20, and 25 reps.

The first time the user performs a new exercise he/she must do one set of reps of that exercise with a weight he/she figures they can complete between 5 and 15 reps before the muscle reaches total fatigue until the next repetition cannot be completed. After completing the set the user registers the weight (W) used and the Repetitions completed (CR). The program calculates the Coefficient datapoint on the Baseline Strength Curve using the Baseline Strength Curve Algorithm appropriate for the User's Profile and the Baseline Strength Value for that exercise.

The repetition targets of 20, 5, 15 and 10 for week 1 are entered. The repetition targets for week 2 of 10, 15, 20, and 25 are entered. Based on the above information the system calculates the Ideal Target Weight (ITW) for each of the sets, given their respective target repetitions (TR). Based on the weights or resistance available at the user's gym, he/she inputs the Available Weight Used (AWU) as near to the system's generated ITW and begins performing the exercises in the sequence prescribed by his/her workout plan with that weight.

The user then performs as many repetitions as possible until reaching total muscle fatigue for set 1, then inputs the number of repetitions completed as CR. After a prescribed west period of 2 to 3 minutes he/she repeats the same process for sets 2, 3 and 4 and inputs the number of reps achieved. This workout plan calls for the same exercises be performed the following week, but with sets with different target repetitions (TR) as mentioned above—10, 15, 20, and 25.

Prior to the person starting the second week of exercises, the system updates the BSV, with the result of the previous week's workout. This uses the strength level achieved in the first week's workout as a baseline for the second week's workout. If the person exceeds the number of Ideal Target Weight (ITW) with the new value of Available Weight Used (AWU), the system will automatically register this as an increase in the BSV and increase the ITW weight for the next training session. If the person underperforms, the BSV will decrease and the system will adjust the ITW down for the next training session. The user can follow his or her strength progression referring to the Total Training values in columns BE and BF, which show the amount of weight "moved" in performing the specific exercise on that training day.

The Baseline Strength Coefficient and Baseline Strength Curve Algorithm is personalized. Every individual has a different physiologic composition, age, sex, training background, history of injuries and an infinite number of other differences which differentiates him/her from all the other people in the world. These differences may be substantial enough to cause his/her strength curve profile to diverge from the Baseline Strength Curve Algorithm initially used by the system based on the provided User Profile.

In the case a persons Achieved Strength Coefficients for any given exercise deviate over time from the Baseline Strength Coefficient, the system will identify this abnormality and proceed to test and adjust the individual's performance data and create an Individual Users Strength Coefficient for the user. This is done for the full range of repetitions performed in executing the given exercise. The coefficient is adjusted, and from the resulting new strength coefficients in different rep values, an Individual Users Algorithm for the user and the specific exercise is generated. This is used as the algorithm to project the Baseline Strength Coefficient, which in turn generates the Ideal Target Weight for the user when performing the that specific exercise with a given number of Target Repetitions. The personalized strength curve evolves and changes form as the user's strength changes. The curve automatically adapts to the user's strength progression and muscle development.

Figures 15, 16:
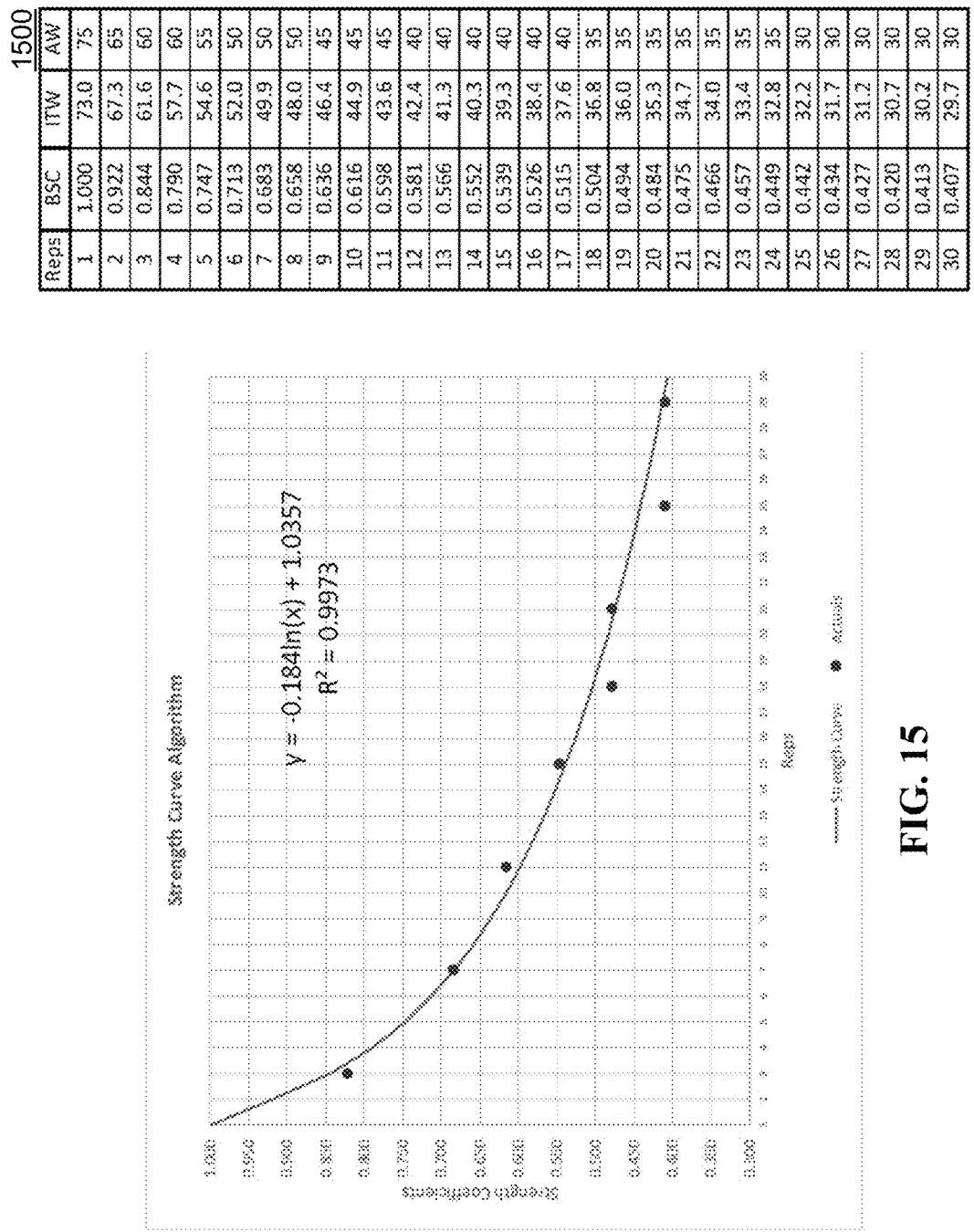
FIG. 15 is a strength curve graph with eight rep datapoints utilized to design a Personalized or Group Specific Strength Curve, in accordance with the present invention
FIG. 16 is a table depicting available weight approximations generated from an ideal target weight generation from the graph in FIG. 15, in accordance with the present invention.
Figure 17:
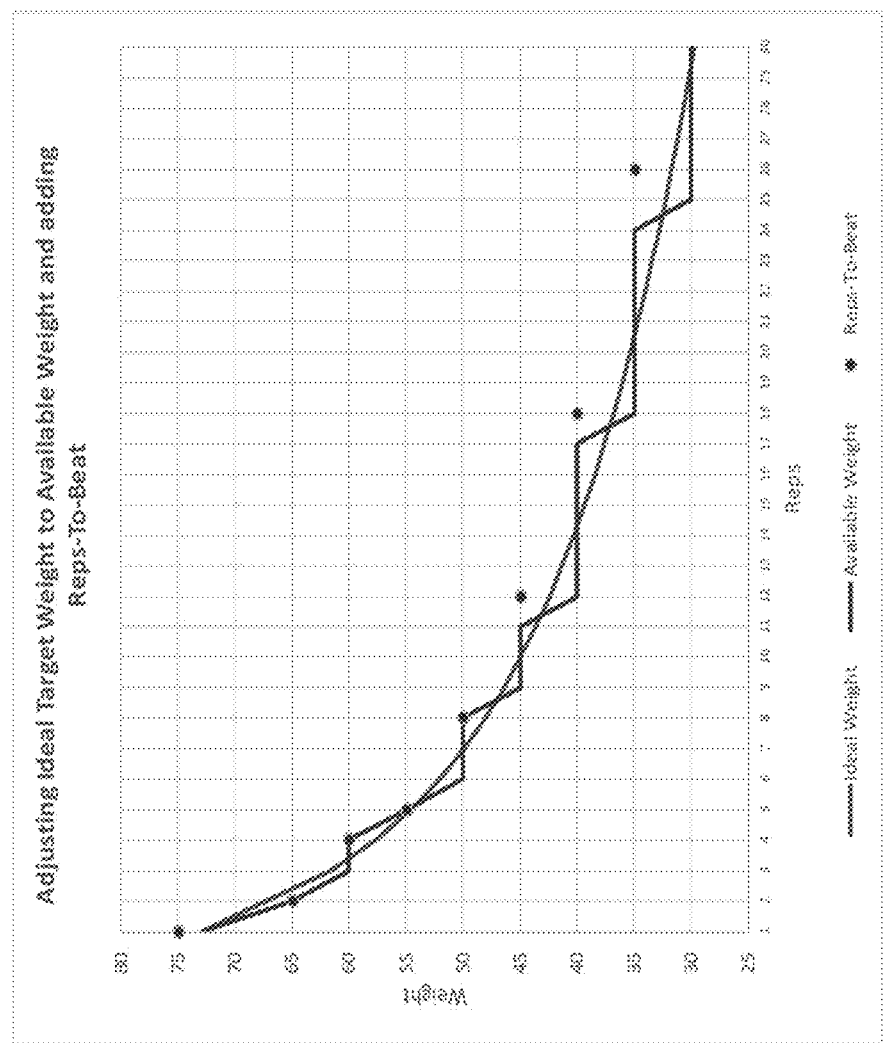
FIG. 17 is a graph depicting steps when an available weight will correspond to a range of target repetitions, in accordance with the present invention.

Additionally and with reference to FIGS. 15-17, once eight or more Actual data points have been gathered for a given exercise a Strength Curve Algorithm can be calculated from Log, Power, Exponential or Polynomial curve fitting methods. The formula with the highest coefficient of determination (R squared), as best seen in FIG. 15, can then be used to calculate the strength coefficients for any given number of reps. The Y-Intercept for the exercise multiplied by any given Strength Coefficient for any number of Repetitions will return the Ideal Target Weight (ITW), which can be exemplified and best seen in the chart 1500 in FIG. 16.

Weights and resistance values found in gyms normally increase by single pound units for lighter weights/resistance, five-pound units for medium weight/resistance, and ten- or twenty-pound units for heavier weights/resistances. Rarely do weights in gyms perfectly match the calculated ITW. In these cases, rounding up or down to the nearest Available Weight (AW) is necessary. Consequently, "steps" are created where a given AW will correspond to not one, but a range of Target Repetitions as seen in the graph depicted in FIG. 17. As a user's muscle strength increases with training, the user will find that he or she will be able to complete more repetitions with a given weight/resistance. Once the maximum number of reps with a given weight are achieved, e.g., 17 Reps with 40 Lbs. from the graph in FIG. 17, the System will increase the weight/resistance to the next heavier Available Weight (AW) for the next training session. As new data points are added after sets of an exercise are completed and registered, older data points are deleted and the Strength Curve Algorithm, BSC, ITW and AW are updated with recent information for the next training session.

As discussed above, ascertaining the reps reached to obtain muscle failure is utilized by the aforementioned algorithm and software application on the mobile electronic device 110. However, the reps obtained for any given exercise set may also be beneficially utilized to project the target or projected weight and reps needed to obtain a user's exercise objective.

More specifically, the system and method (like described above) will involve having the user select a weight to have an initial evaluation or otherwise project a weight to cause the user to reach muscle failure. In preferred embodiments, in the number of repetitions mid-way in the range of repetitions of his/her training objective. If the user's training objective is to gain Strength, his/her normal training range will be from 1 to 5 reps, therefore a weight projected to max out at 3 Target Repetitions (TR) should be used for the test. If the user's training objective is Hypertrophy, his/her normal training range will be from 6 to 12 reps, therefore a weight projected to max out at 9 Target Repetitions (TR) should be used for the test. If the user's training objective is Endurance, his/her normal training range will be from 13 or more reps, therefore a weight projected to max out at 22 Target Repetitions (TR) should be used for the test.

With the data gathered from this test, the system can fine-tune the projected reps-to-beat (RTB) for each set of repetitions. The number of RTBs that can be expected for each additional set, using the same weight, will naturally decrease and the individuals fatigue curve can further fine tune the RTB projected by this invention.

Figures 18, 19:
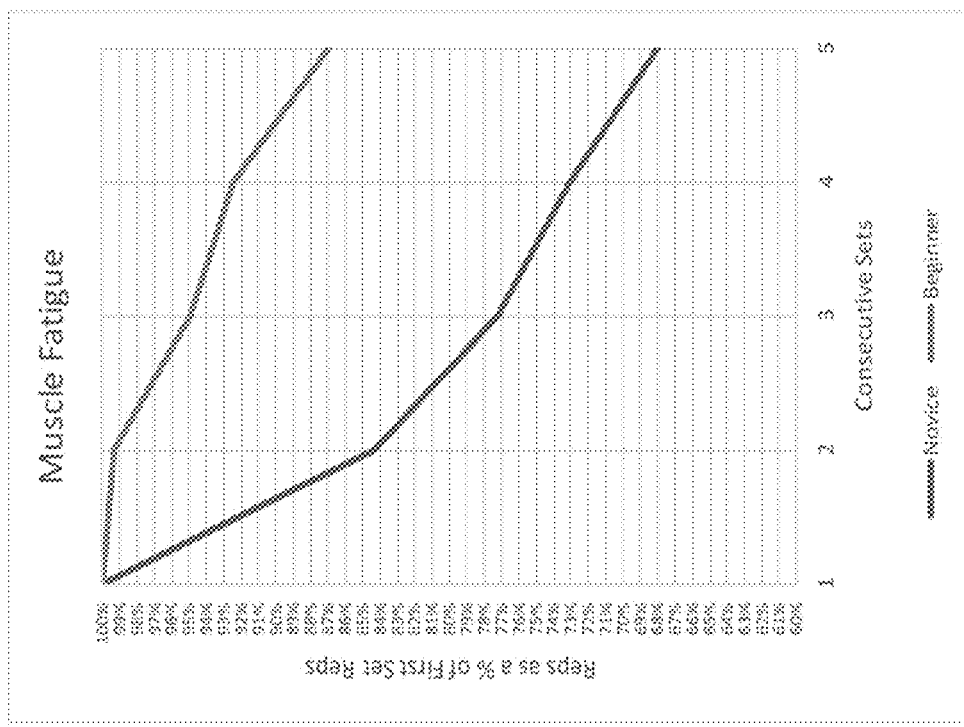
FIG. 18 is a graph depicting exemplary test results for a fatigue testing protocol associated with an exercise routine, in accordance with one embodiment of the present invention.
FIG. 19 is a table depicting reps-to-beat (RTB) multiplier, in accordance with one embodiment of the present invention.
Figure 20:
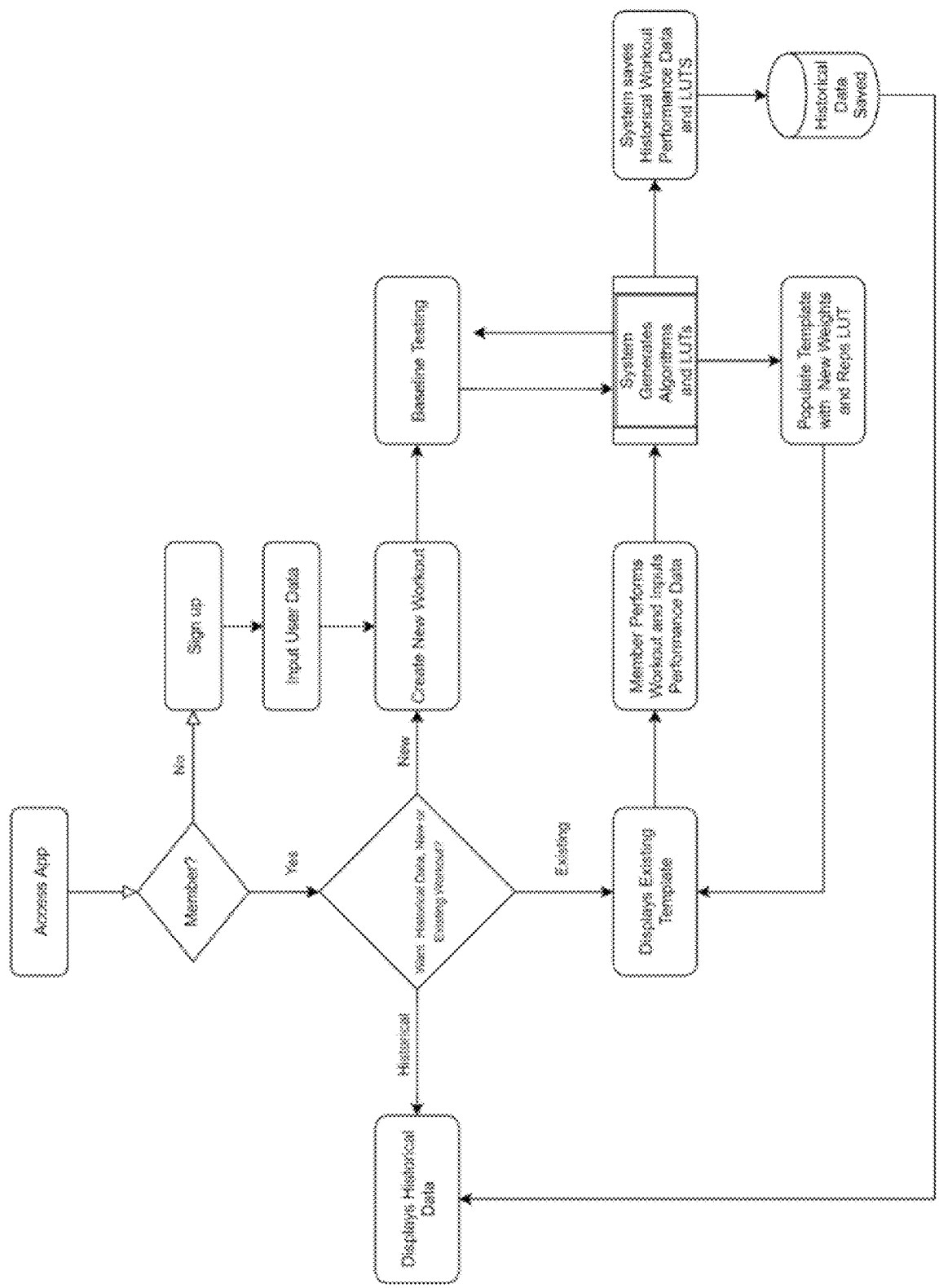
FIG. 20 depicts an exemplary process flow diagram reflecting computer-implemented and resistance-implemented method for recommending an ideal number of repetitions and an ideal target resistance value for an exercise routine in accordance with one embodiment of the present invention.
Figure 21:
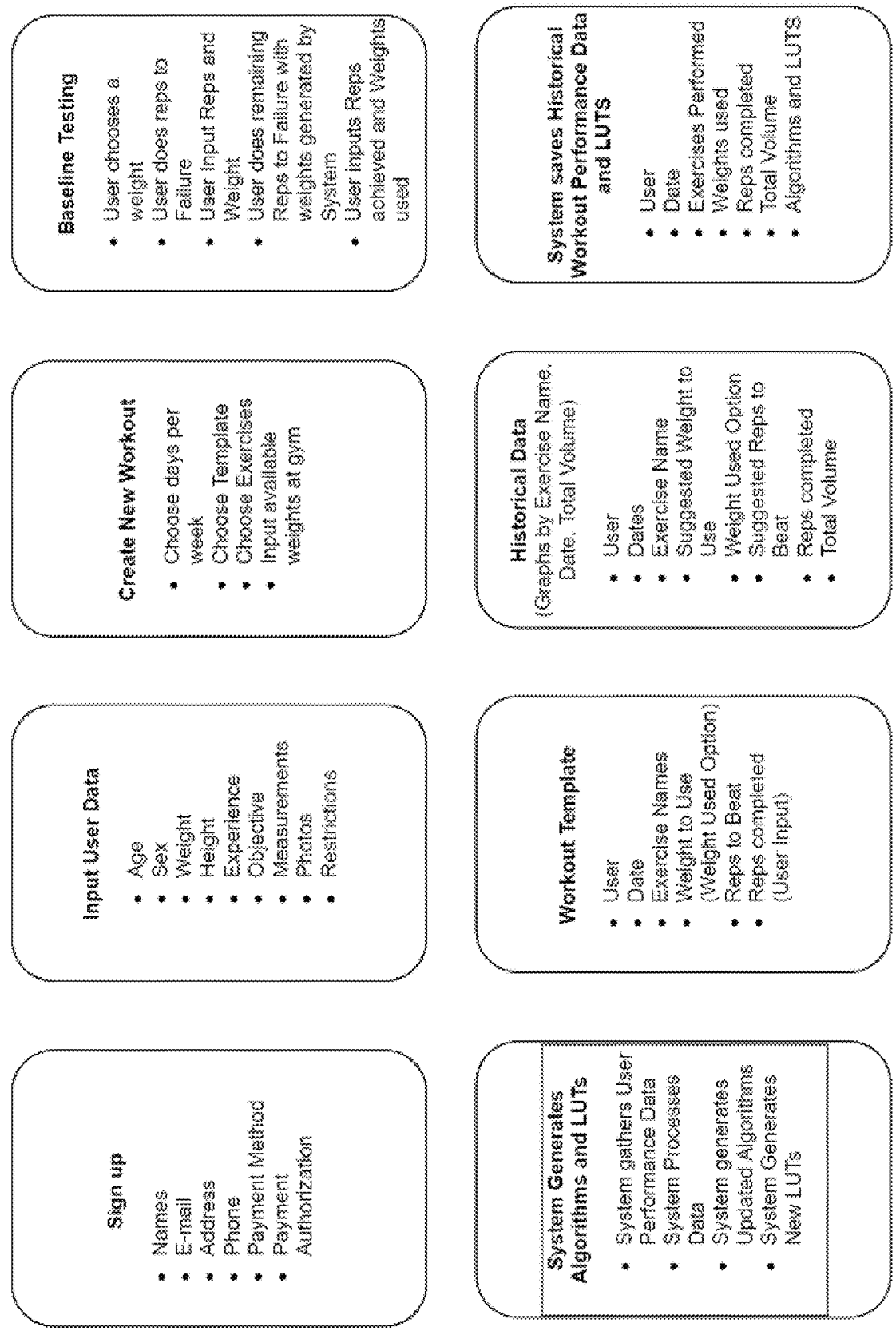
FIG. 21 depicts tables describing features associated with steps depicted in the process flow diagram in FIG. 20.

Over time, with the input from various tests, the system will also be able to determine the gain in resistance of the user's muscles based on his/her chosen exercise workout plan. The graph depicted in FIG. 18 depicts exemplary results of fatigue testing for the exercise routine, bicep curls, performed by a 24-year old individual who had never trained with weights or resistance. FIG. 18 depicts the results of the testing before training began (Novice) and one year (Beginner) after training three days a week using the RTB system of determining the proper Weight and Target Reps method of this invention. As a Novice the number of reps, the user reflected in FIG. 18 was able to complete in the $5^{th}$ set was 68% of the number of reps he achieved in the $1^{st}$ set. One year later he was able to complete 87% of the reps of he achieved in the $1^{st}$ set.

As depicted in FIG. 19, in order to adapt to the user's individual rate of muscle strength that increases for a given muscle, the computer-implemented method and system identifies the rate that the user's historical muscle strength increases from training session to training session and automatically generates the RTB multiplier based on the historical data. This multiplier is then used to increase the TR to the RTB target. In the example at the right a Reps-To-Beat (RTB) Multiplier of 110% increased all TR values by 10%.

As such, a user choosing to apply the RTB functionality in developing a training routine for a given muscle will be informed by the system what Available Weight (AW) to use and the targeted number of Reps-To-Beat (RTB) based on his/her training objective. The user must always try to reach or exceed the prescribed number of RTB for the chosen weight.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the above described features.

What is claimed is:

1. A computer-implemented and resistance-implemented method for recommending an ideal number of repetitions and an ideal target resistance value for an exercise routine, the method comprising the steps:

providing at least one resistance structure with a resistance value and operably configured to be manipulated by a user for an exercise routine;

providing a mobile electronic device of the user with a software application resident thereon, the mobile electronic device operably configured to communicatively couple with a server computer over a network, the mobile electronic device of the user and the server computer each having a processor and memory operably coupled thereto;

initiating the software application to generate a user interface on the mobile electronic device;

manipulating the at least one resistance structure by the user until a muscle fatigue is reached employing a recommended proper resistance structure use protocol for the exercise routine and ascertaining a number of initial completed repetitions associated with the resistance value;

utilizing the number of initial completed repetitions on the user interface of the software application to generate, with one of a plurality of user-data defined y-intercept approximation functions to generate a baseline strength value;

utilizing the baseline strength value on the user interface of the software application to generate a plurality of ideal target weight values utilizing the one of the plurality of user-data defined y-intercept approximation functions, each involving a plurality of desired target repetition values; and manipulating by the user, during a plurality of subsequent sets involving the recommended proper resistance structure use protocol for the exercise routine, the at least one resistance structure associated with the plurality of ideal target weight values, respectively, that are each rounded to the nearest whole number and for the greater of the plurality of user-selected desired target repetition values or until a muscle fatigue is reached to generate second completed repetition values for each of the plurality of subsequent sets.

2. The computer-implemented and resistance-implemented method according to claim 1, further comprising:

after the plurality of desired target repetition values are generated with the plurality of ideal target weight values, generate a reps-to-beat (RTB) multiplier that is multiplied by each of the plurality of desired target repetition values and wherein said result of the multiplication respectively replacing the plurality of desired target repetition values before the user manipulates the at least one resistance structure in the plurality of subsequent sets.

3. The computer-implemented and resistance-implemented method according to claim 1, further comprising:

directly after initiating the software application to generate the user interface on the mobile electronic device, select a user-desired strength objective on the user interface dictating an amount for the number of initial completed repetitions associated with the resistance value.

4. The computer-implemented and resistance-implemented method according to claim 3, wherein:
the user-desired strength objective includes various targeted repetition ranges different from one another on the user interface, the amount for the number of initial completed repetitions associated with the resistance value of a median value within each respective targeted repetition ranges.

5. The computer-implemented and resistance-implemented method according to claim 1, further comprising:
utilizing the number of initial completed repetitions on the user interface of the software application to generate, with one of the plurality of user-data defined y-intercept approximation functions, a baseline strength coefficient, the resistance value divided by the baseline strength coefficient to generate the baseline strength value.

6. The computer-implemented and resistance-implemented method according to claim 1, wherein:
the generated plurality of ideal target weight values utilizing the one of the plurality of user-data defined y-intercept approximation functions are user-selected.

7. The computer-implemented and resistance-implemented method according to claim 1, further comprising:
plotting the rounded plurality of ideal target weight values with respect to the second completed repetition values for each of the plurality of subsequent sets to generate another of the plurality of user-data defined y-intercept approximation functions dictated by a highest coefficient of determination.

8. The computer-implemented and resistance-implemented method according to claim 1, wherein the another of the plurality of user-data defined y-intercept approximation functions consist essentially of:
a logarithmic function, a quadratic function, and a power function.

9. The computer-implemented and resistance-implemented method according to claim 8, wherein:
the one of a plurality of y-intercept approximation functions is a natural logarithmic function.

10. The computer-implemented and resistance-implemented method according to claim 9, wherein:
the natural logarithmic function is $x\ln(ICR)+b$, wherein ICR is the number of initial completed repetitions associated with the resistance value.

11. The computer-implemented and resistance-implemented method according to claim 9, further comprising:
generating a strength curve based on the completed repetitions, and the resistance value of the resistance structure, whereby the repetitions comprise a user-defined x-intercept variable, and the weight values comprise a user-data defined y-intercept variable.

12. The computer-implemented and resistance-implemented method according to claim 1, wherein the resistance structure further comprises:
at least one free-weight structure with the resistance value and operably configured to be lifted by a user for the exercise routine.

13. The computer-implemented and resistance-implemented method according to claim 12, wherein:
the recommended proper resistance structure use protocol comprises a bicep curl motion using a dumbbell for an arm curl, or a 90-degree extension motion for a leg curl.

14. The computer-implemented and resistance-implemented method according to claim 1, wherein:
the number of initial completed repetitions associated with the resistance value comprises 5 to 20 repetitions.

15. The computer-implemented and resistance-implemented method according to claim 1, further comprising:
utilizing the number of initial completed repetitions, and the resistance value of the at least one resistance structure, on the user interface of the software application to generate, with one of a plurality of user-data defined y-intercept approximation functions, a baseline strength coefficient, the resistance value divided by the baseline strength coefficient to generate a baseline strength value.

16. The computer-implemented and resistance-implemented method according to claim 1, wherein:
the baseline strength coefficient is generated on the user interface of the software application with at least one of a look-up table and a completed repetition input field.

17. A computer-implemented and resistance-implemented method for recommending an ideal number of repetitions and an ideal target resistance value for an exercise routine, the method comprising the steps:
providing at least one resistance structure with a resistance value and operably configured to be manipulated by a user for an exercise routine;
providing a mobile electronic device of the user with a software application resident thereon, the mobile electronic device operably configured to communicatively couple with a server computer over a network, the mobile electronic device of the user and the server computer each having a processor and memory operably coupled thereto;
initiating the software application to generate a user interface on the mobile electronic device;
manipulating the at least one resistance structure by the user until a muscle fatigue is reached employing a recommended proper resistance structure use protocol for the exercise routine and ascertaining a number of initial completed repetitions associated with the resistance value;
utilizing the number of initial completed repetitions on the user interface of the software application to generate, with one of a plurality of user-data defined y-intercept approximation functions to generate a baseline strength value;
utilizing the baseline strength value on the user interface of the software application to generate a plurality of ideal target weight values utilizing the one of the plurality of user-data defined y-intercept approximation functions, each involving a plurality of desired target repetition values;
after the plurality of desired target repetition values are generated with the plurality of ideal target weight values, generate a reps-to-beat (RTB) multiplier that is multiplied by each of the plurality of desired target repetition values and wherein said result of the multiplication respectively replacing the plurality of desired target repetition values; and
manipulating by the user, during a plurality of subsequent sets involving the recommended proper resistance structure use protocol for the exercise routine, the at least one resistance structure associated with the plurality of ideal target weight values, respectively, that are each rounded to the nearest whole number and for the greater of the plurality of user-selected desired target repetition values or until a muscle fatigue is reached to generate second completed repetition values for each of the plurality of subsequent sets.

18. A computer-implemented and resistance-implemented method for recommending an ideal number of repetitions and an ideal target resistance value for an exercise routine, the method comprising the steps:
providing at least one resistance structure with a resistance value and operably configured to be manipulated by a user for an exercise routine;
providing a mobile electronic device of the user with a software application resident thereon, the mobile electronic device operably configured to communicatively couple with a server computer over a network, the mobile electronic device of the user and the server computer each having a processor and memory operably coupled thereto;
initiating the software application to generate a user interface on the mobile electronic device;
manipulating the at least one resistance structure by the user until a muscle fatigue is reached employing a recommended proper resistance structure use protocol for the exercise routine and ascertaining a number of initial completed repetitions associated with the resistance value;
utilizing the number of initial completed repetitions on the user interface of the software application to generate, with one of a plurality of user-data defined y-intercept approximation functions to generate a baseline strength value; and
utilizing the baseline strength value to generate a plurality of ideal target weight values utilizing the one of the plurality of user-data defined y-intercept approximation functions, each involving a plurality of desired target repetition values.

19. The computer-implemented and resistance-implemented method according to claim 18, further comprising:
manipulating by the user, during a plurality of subsequent sets involving the recommended proper resistance structure use protocol for the exercise routine, the at least one resistance structure associated with the plurality of ideal target weight values, respectively, for the greater of the plurality of user-selected desired target repetition values or until a muscle fatigue is reached to generate second completed repetition values for each of the plurality of subsequent sets.

20. The computer-implemented and resistance-implemented method according to claim 19, further comprising:
after the plurality of desired target repetition values are generated with the plurality of ideal target weight values, generate a reps-to-beat (RTB) multiplier that is multiplied by each of the plurality of desired target repetition values and wherein said result of the multiplication respectively replacing the plurality of desired target repetition values before the user manipulates the at least one resistance structure in the plurality of subsequent sets.

21. The computer-implemented and resistance-implemented method according to claim 19, wherein:
the generated plurality of ideal target weight values utilizing the one of the plurality of user-data defined y-intercept approximation functions are user-selected.

* * * * *